US012154661B2

(12) United States Patent
Allyn-Feuer et al.

(10) Patent No.: US 12,154,661 B2
(45) Date of Patent: Nov. 26, 2024

(54) METHOD AND APPARATUS FOR ANALYSIS OF CHROMATIN INTERACTION DATA

(71) Applicant: THE REGENTS OF THE UNIVERSITY OF MICHIGAN, Ann Arbor, MI (US)

(72) Inventors: Ari Allyn-Feuer, Ann Arbor, MI (US); Brian D. Athey, Ann Arbor, MI (US); Gerald A. Higgins, Ann Arbor, MI (US); Alex Ade, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 1111 days.

(21) Appl. No.: 16/359,385

(22) Filed: Mar. 20, 2019

(65) Prior Publication Data
US 2019/0295684 A1    Sep. 26, 2019

Related U.S. Application Data

(60) Provisional application No. 62/646,433, filed on Mar. 22, 2018.

(51) Int. Cl.
G16B 15/00    (2019.01)
G16B 20/00    (2019.01)
G16B 40/00    (2019.01)

(52) U.S. Cl.
CPC .............. *G16B 15/00* (2019.02); *G16B 20/00* (2019.02); *G16B 40/00* (2019.02)

(58) Field of Classification Search
CPC ........ G16B 45/00; G16B 15/00; G16B 15/20; G16B 15/10; G16B 40/00; G16B 20/00
See application file for complete search history.

(56) References Cited

U.S. PATENT DOCUMENTS

| | | | |
|---|---|---|---|
| 9,708,648 | B2 | 7/2017 | Dekker et al. |
| 2014/0371078 | A1 | 12/2014 | Abdueva |
| 2016/0019338 | A1 | 1/2016 | Chudova et al. |
| 2016/0232291 | A1* | 8/2016 | Kyriazopoulou-Panagiotopoulou .... G06F 19/22 |
| 2017/0220735 | A1 | 8/2017 | Duenwald et al. |

FOREIGN PATENT DOCUMENTS

| | | | | |
|---|---|---|---|---|
| CN | 103403182 | A | 11/2013 | |
| CN | 103646192 | A | 3/2014 | |
| WO | WO 2009/155443 | A2 * | 12/2009 | ............... C12Q 1/68 |
| WO | WO-2012/071621 | A1 | 6/2012 | |

OTHER PUBLICATIONS

Stansfield, John C., Dozmorov, Mikhail G. HiCcompare: a method for joint normalization of Hi-C datasets and differential chromatin interaction detection (2017) bioRxiv 147850; doi: https://doi.org/10.1101/147850 (Year: 2017).*
Lajoie BR, Dekker J, Kaplan N. The Hitchhiker's guide to Hi-C analysis: practical guidelines. Methods. Jan. 15, 2015;72:65-75. doi: 10.1016/j.ymeth.2014.10.031. Epub Nov. 6, 2014. PMID: 25448293; PMCID: PMC4347522. (Year: 2015).*
Yardimci, G.G., Noble, W. Software tools for visualizing Hi-C data. Genome Biol 18, 26 (2017). https://doi.org/10.1186/s13059-017-1161-y (Year: 2017).*
Wang, Yang, et al. "A novel method to identify topological domains using Hi-C data." Quantitative Biology 3 (2015): 81-89. (Year: 2015).*
Bonev, Boyan et al. "Multiscale 3D Genome Rewiring during Mouse Neural Development." Cell vol. 171,3 (2017): 557-572.e24. doi: 10.1016/j.cell.2017.09.043 (Year: 2017).*
Caleb Weinreb, Benjamin J. Raphael, Identification of hierarchical chromatin domains, Bioinformatics, vol. 32, Issue 11, Jun. 2016, pp. 1601-1609, https://doi.org/10.1093/bioinformatics/btv485 (Year: 2016).*
Bonev et al., Multiscale 3D genome rewiring during mouse neural development, Cell, 171:557-72 (2017).
European Patent Application No. 19771887.7, Extended European Search Report, dated Dec. 2, 2021.
Chen et al., De novo deciphering three-dimensional chromatin interaction and topological domains by wavelet transformation of epigenetic profiles, Nucleic Acids Res., 44(11):e106 (Jun. 2016).
International Application No. PCT/US2019/023356, International Search Report and Written Opinion, mailed Jul. 5, 2019.
Benner C, Heinz S et al. Homer (v4.10, May 16, 2018): Software for motif discovery and next generation sequencing analysis. 2018. <http://homer.ucsd.edu/homer/>.
Cohen NM, Olivares-Chauvet P et al. Shaman: bin-free randomization, normalization and screening of Hi-C matrices. BioRxiv 2017. <http://dx.doi.org/10.1101/187203>.
Dixon JR, Selvaraj S, Yue F et al. Topological domains in mammalian genomes identified by analysis of chromatin interactions. *Nature* 485, 376-380 (2012).

(Continued)

*Primary Examiner* — Joseph Woitach
*Assistant Examiner* — Kettip Kriangchaivech
(74) *Attorney, Agent, or Firm* — MARSHALL, GERSTEIN & BORUN LLP

(57) ABSTRACT

To analyze spatial organization of chromatin a computing device may compile genomic element contacts or reads into variable size bins using a binary search tree. The bins may be selected to each represent a different cutsite increment or functional element within a genome, such as a gene, TAD, chromatin state segment, loop domain, chromatin domain, etc. Two sets of bins are selected to generate a squared genome matrix of bin pairs, where each set represent an axis of the matrix. Then a normalization method is applied to the interaction frequencies for the bin pairs having variable size and/or shape to generate normalized interaction frequencies for each bin pair. The normalized interaction frequencies may be used to identify bin pairs having enriched and depleted contacts for a variety of analyses, including the detection of target genes of genomic variants, as well as genome wide analysis of contacts.

17 Claims, 12 Drawing Sheets

(56) References Cited

OTHER PUBLICATIONS

Lieberman-Aiden E, van Berkum NL, Williams L et al. Comprehensive mapping of long-range interactions reveals folding principles of the human genome. *Science*. 326(5950), 289-293. (2009).

Rao SSP, Huntley MH, Durand NC et al. A 3D map of the human genome at kilobase resolution reveals principles of chromatin looping. *Cell*. 159, 1665-1680 (2014).

Cock PJA, Fields CJ et al. The Sanger FASTQ file format for sequences with quality scores, and the Solexa/Illumina FASTQ variants. Nucleic Acids Res. Apr. 2010; 38(6): 1767-1771. doi: 10.1093/nar/gkp1137.

Langmead B, Salzberg SL. Fast gapped-read alignment with Bowtie 2. Nature Methods vol. 9, pp. 357-359 (2012).

Stansfield et al., HiCcompare: an R-package for joint normalization and comparison of HI-C datasets, BMC Bioinformatics, 19(1):279 (2018).

Miele et al., Mapping cis- and trans-chromatin interaction networks using chromosome conformation capture (3C), Methods in Molecular Biology, 454:1-17 (2013).

Australian Examination Report for Application No. 2019240231, dated Apr. 15, 2024.

Chinese Patent Application No. 201980034320, Office Action, dated Jul. 24, 2024.

\* cited by examiner

700

| rsID | Drug | Chr | Begin | End | TAD Num | Contacts | Gene | Candidate Contacts |
|---|---|---|---|---|---|---|---|---|
| rs2857654 | Valproate | chr17 | 33720000 | 35360000 | 1977 | 47 | CCL2 | 1 |
| rs2269577 | Valproate | chr22 | 28040000 | 29080000 | 2245 | 134 | XBP1 | 2 |
| rs3764028 | Both | chr12 | 13320000 | 14720000 | 1567 | 3 | GRIN2B | 0 |
| rs7980427 | Ketamine | chr12 | 108800000 | 109360000 | 1636 | 46 | DAO | 2 |
| rs1543927 | Ketamine | chr15 | 74040000 | 75000000 | 1832 | 218 | PPCDC | 3 |
| rs7184748 | Ketamine | chr16 | 9160000 | 10920000 | 1862 | 48 | GRIN2A | 0 |
| rs11083595 | Ketamine | chr19 | 38400000 | 40920000 | 2112 | 682 | CYP2B6 | 9 |
| rs28439297 | Ketamine | chr22 | 41920000 | 43480000 | 2258 | 609 | CYP2D6 | 8 |
| rs3822158 | Ketamine | chr4 | 157080000 | 159360000 | 693 | 5 | GLRB | 0 |
| rs17161937 | Ketamine | chr7 | 98880000 | 100320000 | 1063 | 388 | CYP3A43 | 4 |
| rs34547970 | Ketamine | chr9 | 136840000 | 137800000 | 1343 | 172 | GRIN1 | 4 |
| rs12248560, rs77957608, rs61886222 | Ketamine | chr10 | 94240000 | 95440000 | 1418 | 206 | CYP2C9, CYP2C19 | 5 |
| rs71311904 | Ketamine | chr11 | 27480000 | 29360000 | 1472 | 73 | BDNF | 2 |

FIG. 7A

METHOD AND APPARATUS FOR ANALYSIS OF CHROMATIN INTERACTION DATA

CROSS-REFERENCE TO RELATED APPLICATIONS

This application claims priority to and the benefit of the filing date of provisional U.S. Application Ser. No. 62/646,433, filed on Mar. 22, 2018, entitled "Method and Apparatus for Analysis of Chromatin Interaction Data," the entire disclosure of which is hereby expressly incorporated by reference herein.

FIELD OF THE INVENTION

The present application relates to chromatin interaction analysis and, more specifically, to a method and system for utilizing statistical techniques to efficiently identify contacts of genomic elements using variable size bins.

BACKGROUND

Today, genomic element contacts are mapped using Hi-C sequencing or other similar methods, such as Genome Architecture Mapping, ChIA-PET, 4C, 5C, Combi-C, Micro-C, etc. In such methods, paired-end sequencing reads represent pairs of genomic locations which have spatial contact in the bio-cellular sample which was processed to yield the Hi-C sequencing library. A plurality of such paired end reads are compiled into a map or frequency matrix representing the frequency with which pairs of genomic locations spatially interact.

To perform the mapping, datasets are compiled into bins of fixed size which are evenly-sized portions of the genome contiguous to each other. However, this method requires a choice of fixed resolution, which carries with it inherent limitations. At low resolution, loci of interest are combined with unrelated loci, while other loci are split in half. Genes are often regulated by enhancer elements which are very distant from them in sequence space, referred to as distal-cis, or on different chromosomes, referred to as trans. However, such methods do a poor job of detecting distal enhancer interactions due to data sparsity. Trans and distal cis interactions suffer from severe data sparsity, as read pairs in a linear genome are mapped into a squared genome whose area is over nine million squared megabases (Mb). At high resolution, the method is extremely memory intensive and requires significant computational resources.

Moreover, read densities vary by five orders of magnitude with genomic distance and the majority of measured interactions are concentrated along the axis. Thus with fixed bins, fine resolutions will result in a genome-wide matrix over 99.9% of whose entries are empty, while coarse resolutions will completely fail to benefit from the mediation of long range contacts by functional elements, chopping them into pieces and combining them with adjacent sequence regions and thereby dissipating the very signal investigators wish to detect.

Topologically associating domains (TADs) have been identified as potent spatial and functional genomes. The division of approximately 80% of the sequence length of the human genome into approximately 2500 TADs is remarkably robust, being largely conserved between cell types in the human body, between different humans, and under disease states. TADs also function as replication domains. Moreover, TADs mediate long range spatial interactions: the contact frequency in any given portion of the squared genome will more closely correlate with a more sequence-distant portion which is in the same TAD pair than a sequence-proximal portion spanning TAD boundaries.

Recent work has begun to address the disadvantages of fixed binning. The SHAMAN package dispenses with fixed binning and matrix compiling and takes a different approach to contact detection. It uses a sparse matrix at base pair resolution, and then generates a randomized matrix satisfying distance frequency and marginal coverage criteria sampled from the real matrix. It uses this randomized matrix to compare to the real one, generating p-values which are compared with FDR statistics to address random error in Hi-C matrices. However, the p-values are generated from the Kolmogorov-Smirnov D statistics for the density of the K-nearest-neighbor cluster around each of the individual read pairs in the database. Pairs with a significantly dense K nearest neighbors may be considered enriched. The selection of the K value for a particular experiment thus represents a significant tradeoff between resolution and statistical power, much like the selection of bin sizes in traditional Hi-C compiling.

For distal contacts, the SHAMAN package suffers, because it does not account for the mediation of contacts by large sequence elements. The K nearest neighbors of a particular read pair may not be significantly enriched, while the entire TAD pair in which the read pair sits may be enriched. For a suitable value of K, these will be approximately concordant, but SHAMAN provides no way to choose such a K, which will in any event vary genome wide. In addition, a read pair adjacent to a TAD pair with strong clustering may "stow away" on the sequence-close dense read pairs, generating neighbor-spillover contact detections, just in the manner of fixed binning.

Accordingly, there is a need for a system that maps genomic element contacts precisely in order to maintain high accuracy and reduces memory requirements and computing resources compared to prior systems. There is also need for a system that segments related loci in the same bin and does not split loci in half to detect long range cis and trans interactions mediated by functional elements.

SUMMARY

To map genomic element contacts, a chromatin interaction system obtains a set of genomic elements (e.g., loci) and segments the set into bins of varying sizes. Bins may be selected to include related genomic elements in the same bin and to prevent splitting genomic elements in half. For example, each bin may correspond to a contiguous segment of deoxyribonucleic acid (DNA) sequence, and may represent cutsite increments or functional elements, such as genes, chromatin state segments, loop domains, chromatin domains, topologically associating domains (TADs), etc. Two sets of bins are then selected (e.g., a first set of bins corresponding to chromosome 1 and a second set of bins corresponding to chromosome 8) and placed in an n×m matrix (a squared genome area) to generate a set of bin pairs. Accordingly, the squared genome area may be of variable size and shape. In some embodiments, both sets of bins are the same (e.g., each corresponding to chromosome 1). In any event, the chromatin interaction system identifies pairs of locations corresponding to paired-end reads or other spatially interacting locations (e.g., Chr1:950000 and Chr8:15000) with bin pairs which may contain them, i.e. wherein one of the bins contains one of the loci and the other bin contains the other locus, using a binary search tree, for example.

Then an interaction frequency is generated for each bin pair based on the genomic element contacts within the corresponding bin pair. Additionally, the interaction frequencies are normalized according to the density of pairwise contacts as a function of genomic distance within each bin pair. More specifically, the density of pairwise contacts as a function of genomic distance may be determined to generate a density function. Such a function may be corrected for the GC sequence percentage in the particular bin sequences, the sequence coverage of particular bin sequences within a Hi-C sequencing dataset, or other appropriate factors for use in Hi-C normalization. Then, for a particular bin pair, the density function is integrated over the squared genome area of the bin pair to determine an expected density for the bin pair. The expected density may then be compared to the actual density for the bin pair (i.e., the number of pairwise contacts within the squared genome area of the bin pair) with, e.g., statistical tests such as the Poisson distribution p-value, to which, e.g., Benjamini false discovery rates may be applied, to generate a collection of enriched and depleted chromatin contacts in a manner adjusted for distance (and other features as appropriate), on a local or genome-wide basis. The chromatin interaction system may then provide indications of the bin pairs having, e.g., enriched or depleted contacts for display on a user interface.

In this manner, the enriched or depleted contacts may be used for predicting molecular phenotypes for a subject based on the spatial interactions of loci within their respective genomes. The enriched or depleted contacts may also be used to model 3D and 4D structures of chromosomes, and to identify altered TAD boundaries and spatial interactions in a tissue sample for determining genetic disease or oncology. Moreover, the enriched or depleted contacts may be used for determining if a pair of loci interact with each other in a particular tissue or cell line. Still further, the enriched or depleted contacts may be used to locate trans and distal cis binding partners of functional TADs and construct spatial contact networks. The present embodiments advantageously detect long range contacts that are not found with prior systems using traditional methods, in the same dataset with comparable bins of fixed size and spacing. In an experiment, the present embodiments detected 2.5 times as many significant long-range cis interactions between TADs, compared to traditional methods.

Additionally, by using variable bin sizes, the present embodiments advantageously reduce memory requirements and computing resources to map spatial interactions compared to traditional methods. When using fixed size bins to map spatial interactions as in traditional methods, a resolution must be chosen that is sufficiently high to ensure that the borders of each bin fall within a selected range. For example, when using fixed size bins to map spatial interactions between TADs, a resolution must be selected such that the segment of DNA sequence corresponding to each bin is shorter than the shortest TAD. In other words, if the smallest TAD is 100 kilobases (kB), then the resolution for the fixed size bins must be at most 100 kB. To increase accuracy, the resolution is typically much smaller than the shortest TAD (e.g., 1 kB or 10 kB) and several bins are aggregated. On the other hand, using variable bin sizes, the present embodiments select bins such that each bin represents a different TAD (or other functional element such as a gene, chromatin state segment, loop domain, chromatin domain, etc.) regardless of its length. If for example, the average TAD is 1 megabase (MB) long then the present embodiments may map spatial interactions for the same functional element (TADs) using effectively a 1 MB resolution compared to a 1 kB or 10 kB for mapping spatial interactions between TADs using traditional methods. Thus, the present embodiments are less memory intensive and computationally complex than traditional methods. Where n is the number of read pairs and k the number of bins in a square matrix, the complexity of each step is approximately $O(n)$ for alignment and quality control, $O(n*\log(k))$ for compiling, $O(k)$ for integration, and $O(k^2)$ for statistical control and data output. Each of these steps are described in further detail below with reference to FIG. 8.

In an embodiment, a computer-implemented method for analyzing spatial and temporal organization of chromatin is provided. The method includes obtaining a set of pairwise contacts of genomic elements, segmenting genomic elements into a plurality of bins, where bin sizes for the plurality of bins are non-uniform, identifying a first set of the plurality of bins and a second set of the plurality of bins, and generating a matrix of n×m bin pairs, where n corresponds to the first set of the plurality of bins and m corresponds to the second set of the plurality of bins. The method further includes identifying a subset of pairwise contacts within each of the bin pairs, determining an interaction frequency for each of the bin pairs, normalizing each of the interaction frequencies to generate a normalized interaction frequency for each bin pair, and providing a mapping of chromatin interactions for display on a user interface, including indications of the bin pairs and respective indications of normalized interaction frequencies.

In another embodiment, a computing device for analyzing spatial and temporal organization of chromatin is provided. The computing device includes a communication network, one or more processors, and a non-transitory computer-readable memory coupled to the one or more processors and storing instructions thereon. When executed by the one or more processors, the instructions cause the system to obtain a set of pairwise contacts of genomic elements, segment genomic elements into a plurality of bins, where bin sizes for the plurality of bins are non-uniform, identify a first set of the plurality of bins and a second set of the plurality of bins, and generate a matrix of n×m bin pairs, wherein n corresponds to the first set of the plurality of bins and m corresponds to the second set of the plurality of bins. The instructions further cause the system to identify a subset of pairwise contacts within each of the bin pairs, determine an interaction frequency for each of the bin pairs, normalize each of the interaction frequencies to generate a normalized interaction frequency for each bin pair, and provide, via the communication network, a mapping of chromatin interactions for display on a user interface, including indications of the bin pairs and respective indications of normalized interaction frequencies.

BRIEF DESCRIPTION OF THE DRAWINGS

FIG. 7A depicts an example display of enriched contacts and corresponding loci and/or single nucleotide polymorphisms (SNPs) associated with molecular phenotypes in accordance with the presently described embodiments;

DETAILED DESCRIPTION

Figure 1A:
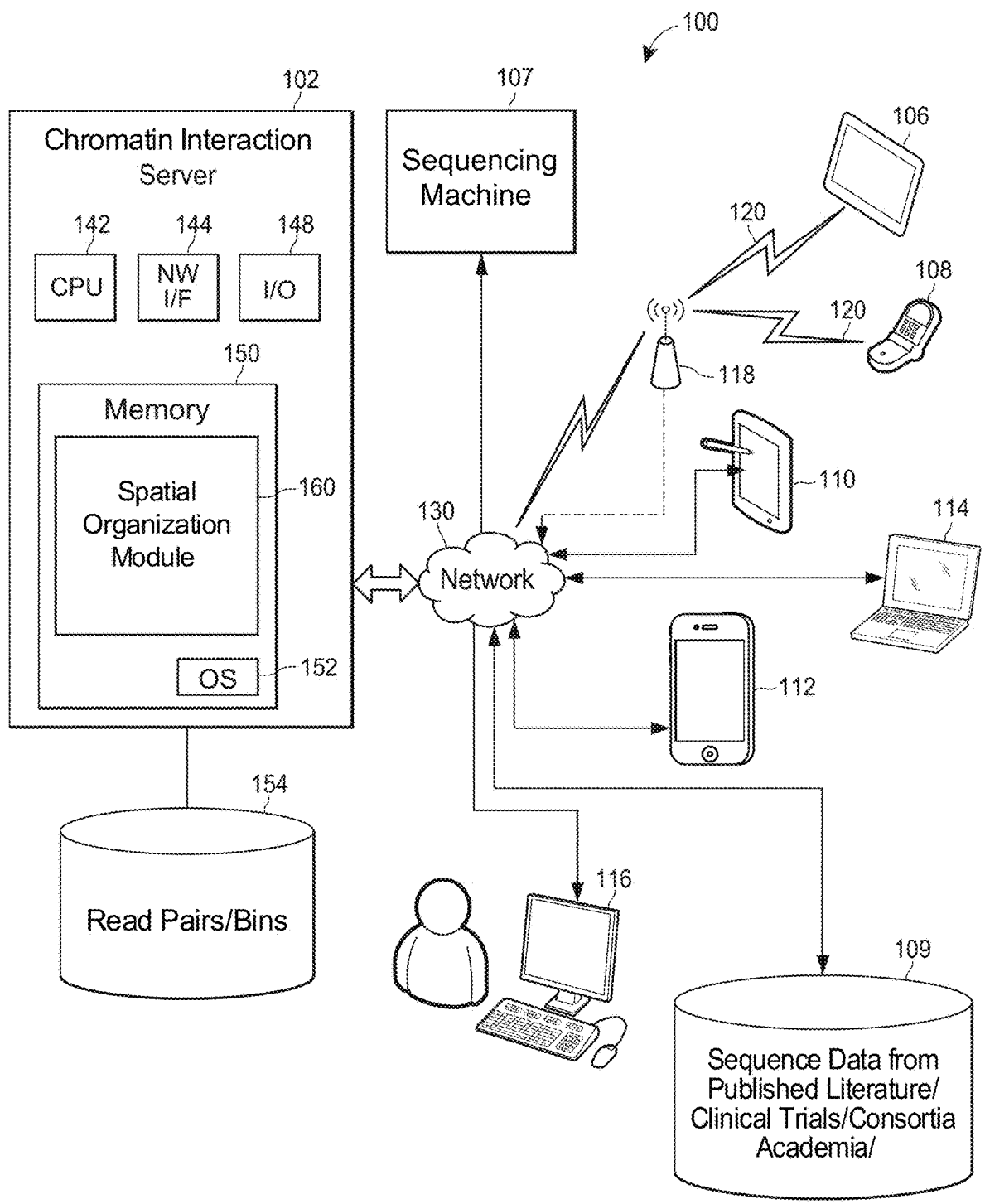
FIG. 1A illustrates a block diagram of a computer network and system on which an exemplary chromatin interaction system may operate in accordance with the presently described embodiments.

Although the following text sets forth a detailed description of numerous different embodiments, it should be understood that the legal scope of the description is defined by the words of the claims set forth at the end of this disclosure. The detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

Accordingly, as used herein, the term "read pair" or "pairwise genomic element contacts" may refer to a pair of loci within respective portions of the genome. For example a read pair may be Chr1:950000, Chr8:15000.

Additionally, as used herein, the term "genomic element" may refer a particular unit of the deoxyribonucleic acid (DNA) sequence. A genomic element may be a read, a locus within a chromosome, a base pair, etc.

The term "bin" as used herein, may refer to a contiguous segment of DNA sequence within the genome of a human or other organism that is considered as a unit for the purposes of a chromatin contact analysis. Such bins may be chosen for a variety of purposes aimed at by particular analyses, and e.g. may include sequence regions corresponding to TADs, interTAD segments, genes, superTADs, subTADs, loop domains, ordinary domains, enhancer and/or promoter bodies, exons, introns, chromatin state segments, restriction enzyme cutsite fragments, genetic engineering insert constructs, translocated elements, LADs, NORs, SARs, MARs, or combinations of these elements.

Furthermore, as used herein, the term "bin pair" may refer to a rectangular region in squared-genome space corresponding to the Cartesian product of two bins represented in linear genome space. This term may also refer to the two bins considered as a pair, rather than the region of squared genome space represented by the pair.

As used herein, the term "subject" may refer to any human or other organism, or combination thereof, whose health, longevity, or other biological outcomes is the object of clinical or research interest, investigation, or effort.

As used herein, the term "pharmacological phenotype" may refer to any discernible phenotype which may have bearing on medical treatment, subject longevity and outcomes, quality of life, etc., in the context of clinical care, management and finance of clinical care, and pharmaceutical and other medical and biomedical research in humans and other organisms. Such phenotypes may include pharmacokinetic (PK) and pharmacodynamic phenotypes (PD) including all phenotypes of rates and characters of absorption, distribution, metabolism, and excretion of drugs (ADME), as well as response to drugs related to efficacy, therapeutic dosages of drugs, half-lives, plasma levels, clearance rates, etc., as well as adverse drug events, adverse drug response and corresponding severities of the adverse drug events or adverse drug response, organ injury, substance abuse and dependence and the likelihood thereof, as well as body weight and changes thereof, mood and behavioral changes and disturbances. Such phenotypes may also include reactions, beneficial and adverse, to combinations of drugs, drugs interactions with genes, sociological and environmental factors, dietary factors, etc. They may also include adherence to a pharmacological or non-pharmacological treatment regime. They may also include medical phenotypes such as the propensity of the subject to contract a certain disease or comorbid condition, outcomes and prognoses of disease, whether the subject will suffer particular symptoms of disease, and subject outcomes like longevity, clinical scores and parameters, test results, health care spending, and other phenotypes.

As used herein, the term "molecular phenotype" may refer to a pharmacological phenotype or to any other phenotype of a human or other organism which is capable of measurement or discernment, at a particular point in time or in retrospect, individually or in the aggregate, and which may be detected, assessed, estimated, or modified, affected, or altered, for any useful purpose.

Generally speaking, techniques for mapping spatial interactions may be implemented in one or several client devices, one or several network servers, or a system that includes a combination of these devices. However, for clarity, the examples below focus primarily on an embodiment in which a chromatin interaction server obtains a set of read pairs or pairwise genomic element contacts such as a pair of loci (e.g., Chr1:950000, Chr8:15000). The chromatin interaction server also obtains a set of bins, which are non-overlapping contiguous segments of DNA. In some embodiments, the set of read pairs and/or set of bins may be obtained from a client device of a researcher or health care professional. For example, the researcher or health care professional may select a particular set of read pairs to analyze. Furthermore, the researcher or health care professional may select a particular set of bins at a particular resolution. For example, the researcher or health care professional may select a set of bins where each bin represents a different TAD. In another example, the researcher or health care professional may select a set of bins where each bin represents a different gene.

In any event, the bins may have variable sizes or sequence lengths and may be used to divide one or more portions of the genome into segments, where each bin represents a cutsite increment or functional element, such as a gene, a chromatin state segment, a loop domain, a chromatin domain, a TAD, etc. (e.g., Chr1:1000-2000). Then the chromatin interaction server selects two sets of bins (e.g., a first set of bins corresponding to Chromosome 2 and a second set of bins corresponding to Chromosome 5, two of the same sets of bins each corresponding to Chromosome 3, etc.). Each set may represent an axis of an n×m squared genome matrix, where the first set includes n bins and the second set includes m bins. Accordingly, the squared genome matrix may include n×m bin pairs, where a bin pair is one entry or rectangle in the squared genome matrix (e.g., Chr1:1000-2000*Chr8:10000-20000). The chromatin interaction server also may assign each read pair to a corresponding bin pair. For example, the read pair Chr1:1010, Chr8:15000 may be assigned to bin pair Chr1:1000-2000*Chr8:10000-20000, because the read pair is within the boundaries of the squared genome region corresponding to the bin pair. In particular, bins and sets of bins may be constructed so as to analyze contacts which are cis, i.e. wherein the bins in a bin pair are located on the same chromosome, or trans, i.e. wherein the bins in a bin pair are located on different chromosomes.

Still further, the chromatin interaction server may determine interaction frequencies for each bin pair based on the density of read pairs within the bin pair. Each interaction frequency may be normalized by calculating a density function for the entire set of read pairs as a function of genomic distance or the distance of two loci (also referred to herein as "reads") from each other within each read pair. Such a function may be corrected for the GC sequence percentage in the particular bin sequences, the sequence coverage of particular bin sequences within a Hi-C sequencing dataset, the density of cutsites within a particular sequence region, or other appropriate factors for use in Hi-C normalization. For each bin pair, the density function may be integrated over the rectangular area of the bin pair to determine an expected density for the bin pair. The expected density for the bin pair may then be compared to the actual density for the bin pair (the density of read pairs within the bin pair) using statistical methods, such as a Poisson distribution p-value, to which, e.g., Benjamini false discovery rates may be applied. Based on the p-values and false discovery rates, the chromatin interaction server may identify the bin pairs having enriched contacts and bin pairs having depleted contacts. Then the chromatin interaction server may provide indications of the bin pairs and indications of their respective normalized interaction frequencies such as p-values to a client device for display. The client device may present a spatial interaction map such as heat map, where bin pairs higher normalized interaction frequencies are represented with darker colors. In other embodiments, the client device may present numerical indications of the normalized interaction frequencies, such as p-values for each bin pair. Accordingly, a health care professional or researcher may review the spatial interaction map or numerical indications on her client device to see the bin pairs having enriched or depleted contacts.

In some embodiments, actual read counts for multiple sets of contacts such as in a bin pair, e.g. corresponding to different bio-cellular systems or different physiological conditions, may be analyzed together. E.g., such systems might constitute two different tissues within the human body, tissue samples from two different individuals, a cell line subjected to a medical treatment as versus a control sample, or multiple cell cycle conditions (e.g., interphase or metaphase) or cellular differentiation states for the same tissue, cell line, or organism. Such an analysis may determine, for example, a set of differential contacts between a pair of sets of contacts, by, e.g., comparing the enriched and depleted contacts from each dataset individually. Differential contacts may also be determined by, e.g., using the multiple sampling distribution of the Poisson or other statistical distribution to generate p-values corresponding to the probability of differential interaction frequencies being observed by chance, which may then be corrected with false discovery rate (FDR) or other methods, as described herein.

Referring to FIG. 1A, an example chromatin interaction system 100 identifies enriched or depleted contacts within bin pairs for a selected set of read pairs and bins. The bin pairs having enriched or depleted contacts may be highlighted and displayed on a researcher or health care professional's client device. For example, the bin pairs having enriched or depleted contacts may be highlighted within a spatial interaction map. The health care professional or researcher may then use the enriched or depleted contacts to predict molecular phenotypes for a subject based on the spatial interactions of loci within their respective genomes. Such predictions may be made using spatial interactions along with other forms of clinical and/or panomics information, using other methods as described elsewhere. The enriched or depleted contacts may also be used to model 3D and 4D structures of chromosomes or genomes within the nucleus of a cell, and to identify altered TAD boundaries and spatial interactions in a tissue sample for determining genetic disease or oncology. Moreover, the enriched or depleted contacts may be used for determining if a pair of loci interact with each other in a particular tissue or cell line.

The chromatin interaction system 100 includes a chromatin interaction server 102 and a plurality of client devices 106-116 which may be communicatively connected through a network 130, as described below. In an embodiment, the chromatin interaction server 102 and the client devices 106-116 may communicate via wireless signals 120 over a communication network 130, which can be any suitable local or wide area network(s) including a WiFi network, a Bluetooth network, a cellular network such as 3G, 4G, Long-Term Evolution (LTE), 5G, the Internet, etc. In some instances, the client devices 106-116 may communicate with the communication network 130 via an intervening wireless or wired device 118, which may be a wireless router, a wireless repeater, a base transceiver station of a mobile telephony provider, etc. The client devices 106-116 may include, by way of example, a tablet computer 106, a sequencing machine 107, a network-enabled cell phone 108, a sequence database 109 including sequence data from published literature, clinical trial, consortia, academia, etc., a personal digital assistant (PDA) 110, a mobile device smart-phone 112 also referred to herein as a "mobile device," a laptop computer 114, a desktop computer 116, wearable biosensors, a portable media player (not shown), a phablet, any device configured for wired or wireless RF (Radio Frequency) communication, etc. Moreover, any other suitable client device that records genomic data for subjects, receives sets of read pairs/bins, or displays indications of enriched contacts may also communicate with the chromatin interaction server 102.

Each of the client devices 106-116 may interact with the chromatin interaction server 102 to provide a selected set of read pairs and/or selected sets of bins. For example, the sequencing machine 107 may generate sequence data which is provided to the chromatin interaction server 102. In another example, the sequence database 109 may provide preexisting sequence data generated from for example, published literature, clinical trial, consortia, academia, etc., to the chromatin interaction server 102. The chromatin interaction server 102 may then identify a set of read pairs and/or sets of bins from the sequence data. Each client device 106-116 may also interact with the chromatin interaction server 102 to receive one or several indications of bin pairs and indications of normalized interaction frequencies for the bin pairs. The indications may be numerical indications and the client device may present the numerical indication via a user interface for display to a health care professional or researcher. The client device may also present a graphical representation of the bin pairs and normalized interaction frequencies, such as a heat map where the squared genome regions corresponding to bin pairs having higher normalized interaction frequencies (e.g., enriched contacts) are highlighted in darker colors.

In an example implementation, the chromatin interaction server 102 may be a cloud based server, an application server, a web server, etc., and includes a memory 150, one or more processors (CPU) 142 such as a microprocessor coupled to the memory 150, a network interface unit 144, and an I/O module 148 which may be a keyboard or a touchscreen, for example.

The chromatin interaction server 102 may also be communicatively connected to a database 154 of read pairs and bins. For example, the database 154 may store a collection of bins across the genome or a portion of the genome, where each bin represents a set of loci corresponding to a TAD (e.g., Chr1:1280000-1840000). In some embodiments, the chromatin interaction server 102 may retrieve a set of read pairs and/or the sets of bins from the database 154. In other embodiments, the set of read pairs and/or the sets of bins are provided by the client device 106-116. In yet other embodiments, the chromatin interaction server 102 may retrieve the bins from the database and a health care professional or researcher may select sets of bins for each axis of the squared genome matrix (e.g., a first set of bins corresponding to Chromosome 1 and a second set of bins corresponding to Chromosome 4).

The memory 150 may be tangible, non-transitory memory and may include any types of suitable memory modules, including random access memory (RAM), read only memory (ROM), flash memory, other types of persistent memory, etc. The memory 150 may store, for example instructions executable of the processors 142 for an operating system (OS) 152 which may be any type of suitable operating system such as modern smartphone operating systems, for example. The memory 150 may also store, for example instructions executable on the processors 142 for a spatial organization module 160. The chromatin interaction server 102 is described in more detail below with reference to FIG. 1B. In some embodiments, the spatial organization module 160 may be a part of one or more of the client devices 106-116, the chromatin interaction server 102, or a combination of the chromatin interaction server 102 and the client devices 106-116.

In any event, the spatial organization module 160 may obtain a set of read pairs and sets of bins from the database 154 and/or the client device 106-116. The spatial organization module 160 may then generate an n×m squared genome matrix using each set of bins as an axis to identify n×m bin pairs. Furthermore, for each bin pair, the spatial organization module 160 may identify a subset of read pairs that corresponds to the bin pair. Then the spatial organization module 160 may identify normalized interaction frequencies for each bin pair by comparing an actual density of read pairs within the bin pair to an expected density based on a density function across all of the read pairs as a function of genomic distance. Such a function may be corrected for the GC sequence percentage in the particular bin sequences, the sequence coverage of particular bin sequences within a Hi-C sequencing dataset, or other appropriate factors for use in Hi-C normalization. The comparison may be performed using various statistical methods to generate a p-value, for example, which may be compared to a confidence threshold to determine whether a particular bin pair has enriched contacts. The spatial organization module 160 may provide indications of the bin pairs and indications of respective normalized interaction frequencies for display on a client device 106-116. The indications may be displayed in a numerical form or in a graphical form, such as in a spatial interaction map, as described in more detail below with reference to FIG. 7.

The chromatin interaction server 102 may communicate with the client devices 106-116 via the network 130. The digital network 130 may be a proprietary network, a secure public Internet, a virtual private network and/or some other type of network, such as dedicated access lines, plain ordinary telephone lines, satellite links, combinations of these, etc. Where the digital network 130 comprises the Internet, data communication may take place over the digital network 130 via an Internet communication protocol.

Figure 1B:
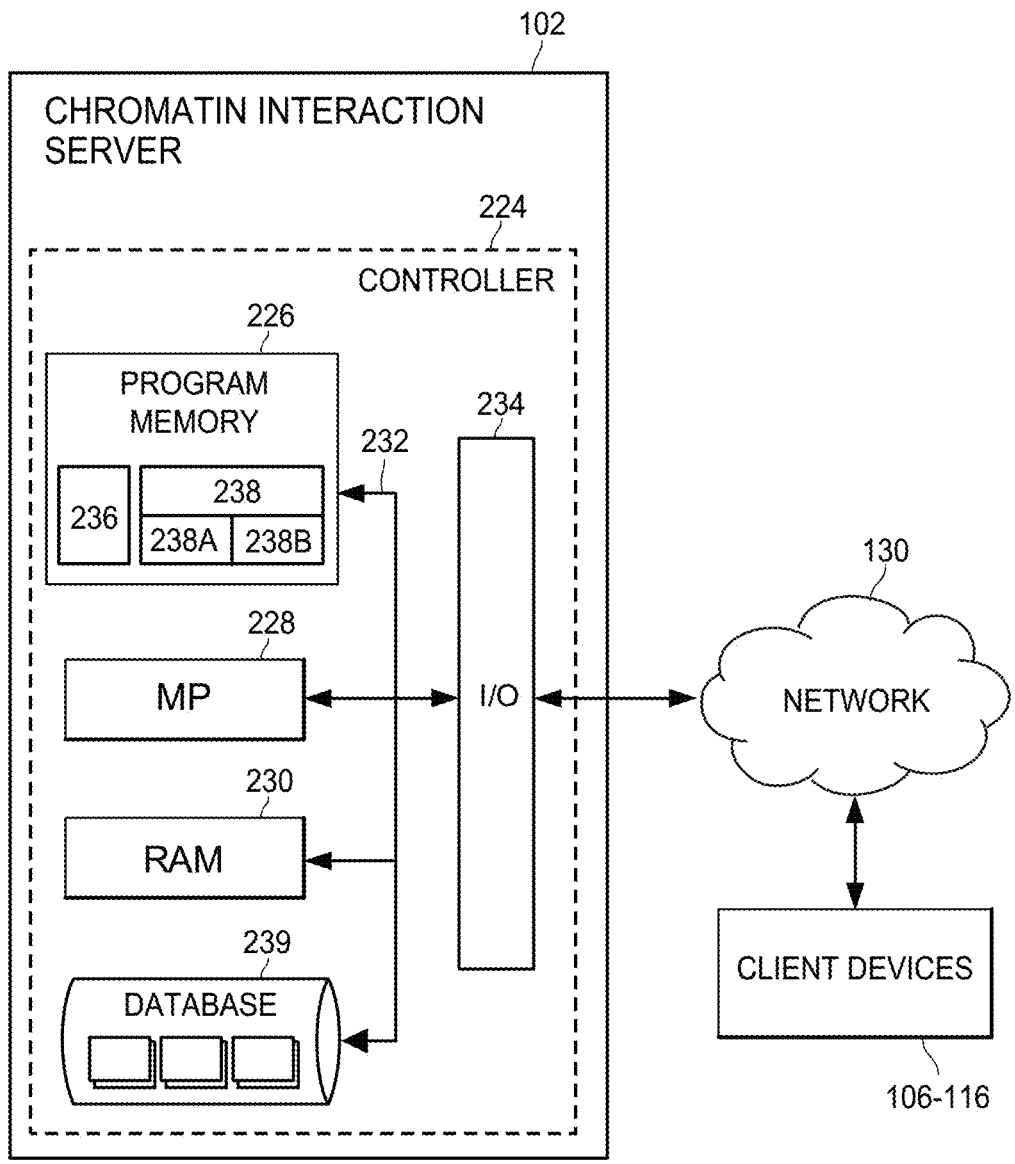
FIG. 1B is a block diagram of an exemplary chromatin interaction server that can operate in the system of FIG. 1A in accordance with the presently described embodiments.

Turning now to FIG. 1B, the chromatin interaction server 102 may include a controller 224. The controller 224 may include a program memory 226, a microcontroller or a microprocessor (MP) 228, a random-access memory (RAM) 230, and/or an input/output (I/O) circuit 234, all of which may be interconnected via an address/data bus 232. In some embodiments, the controller 224 may also include, or otherwise be communicatively connected to, a database 239 or other data storage mechanism (e.g., one or more hard disk drives, optical storage drives, solid state storage devices, etc.). The database 239 may include data such as subject information, read pair data, bin data, spatial interaction mapping templates, web page templates and/or web pages, and other data necessary to interact with users through the network 130. The database 239 may include similar data as the database 154 described above with reference to FIG. 1A.

It should be appreciated that although FIG. 1B depicts only one microprocessor 228, the controller 224 may include multiple microprocessors 228. Similarly, the memory of the controller 224 may include multiple RAMs 230 and/or multiple program memories 226. Although FIG. 1B depicts the I/O circuit 234 as a single block, the I/O circuit 234 may include a number of different types of I/O circuits. The controller 224 may implement the RAM(s) 230 and/or the program memories 226 as semiconductor memories, magnetically readable memories, and/or optically readable memories, for example.

As shown in FIG. 1B, the program memory 226 and/or the RAM 230 may store various applications for execution by the microprocessor 228. For example, a user-interface application 236 may provide a user interface to the chromatin interaction server 102, which user interface may, for example, allow a system administrator to configure, troubleshoot, or test various aspects of the server's operation. A server application 238 may operate to receive a set of read pairs and sets of bins, generate a squared genome matrix of bin pairs, identify normalized interaction frequencies for each bin pair, and provide indications of the bin pairs and indications of normalized interaction frequencies to the health care professional's or researcher's client device 106-116. The server application 238 may be a single module 238 such as the spatial organization module 160 or a plurality of modules 238A, 238B.

While the server application 238 is depicted in FIG. 1B as including two modules, 238A and 238B, the server application 238 may include any number of modules accomplishing tasks related to implementation of the chromatin interaction server 102. Moreover, it will be appreciated that although only one chromatin interaction server 102 is depicted in FIG. 1B, multiple chromatin interaction servers 102 may be provided for the purpose of distributing server load, serving different web pages, etc. These multiple chromatin interaction servers 102 may include a web server, an entity-specific server (e.g. an Apple® server, etc.), a server that is disposed in a retail or proprietary network, etc.

Figure 1C:
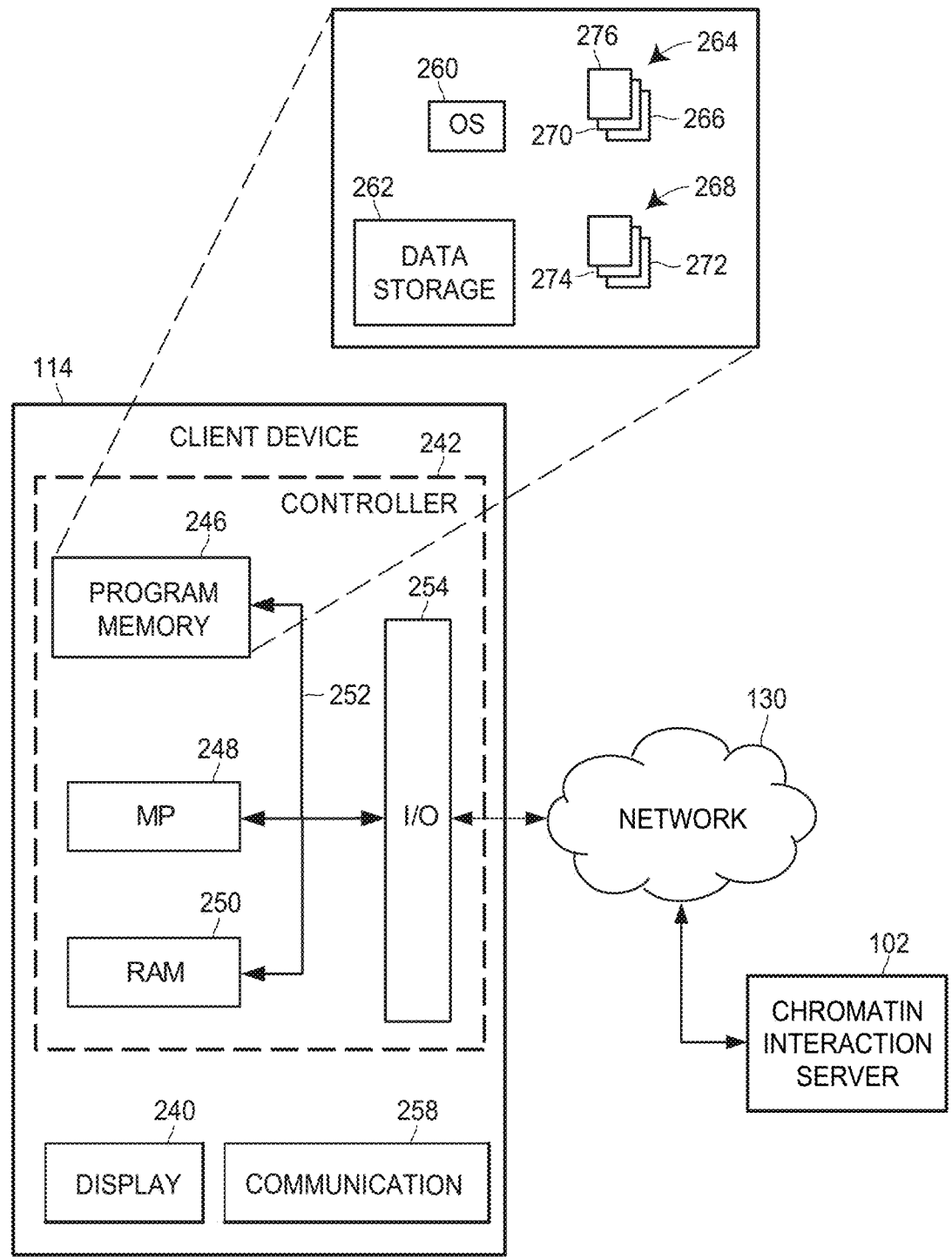
FIG. 1C is a block diagram of an exemplary client device that can operate in the system of FIG. 1A in accordance with the presently described embodiments.

Referring now to FIG. 1C, the laptop computer 114 (or any of the client devices 106-116) may include a display 240, a communication unit 258, a user-input device (not shown), and, like the chromatin interaction server 102, a controller 242. Similar to the controller 224, the controller 242 may include a program memory 246, a microcontroller or a microprocessor (MP) 248, a random-access memory (RAM) 250, and/or an input/output (I/O) circuit 254, all of which may be interconnected via an address/data bus 252. The program memory 246 may include an operating system 260, a data storage 262, a plurality of software applications 264, and/or a plurality of software routines 268. The operating system 260, for example, may include Microsoft Windows®, OS X®, Linux®, Unix®, etc. The data storage 262 may include data such as subject information, application data for the plurality of applications 264, routine data for the plurality of routines 268, and/or other data necessary to interact with the chromatin interaction server 102 through the digital network 130. In some embodiments, the controller 242 may also include, or otherwise be communicatively connected to, other data storage mechanisms (e.g., one or more hard disk drives, optical storage drives, solid state storage devices, etc.) that reside within the laptop computer 114.

The communication unit 258 may communicate with the chromatin interaction server 102 via any suitable wireless communication protocol network, such as a wireless telephony network (e.g., GSM, CDMA, LTE, etc.), a Wi-Fi network (802.11 standards), a WiMAX network, a Bluetooth network, etc. The user-input device (not shown) may include a "soft" keyboard that is displayed on the display 240 of the laptop computer 114, an external hardware keyboard communicating via a wired or a wireless connection (e.g., a Bluetooth keyboard), an external mouse, a microphone for receiving voice input or any other suitable user-input device. As discussed with reference to the controller 224, it should be appreciated that although FIG. 1C depicts only one microprocessor 248, the controller 242 may include multiple microprocessors 248. Similarly, the memory of the controller 242 may include multiple RAMs 250 and/or multiple program memories 246. Although the FIG. 1C depicts the I/O circuit 254 as a single block, the I/O circuit 254 may include a number of different types of I/O circuits. The controller 242 may implement the RAM(s) 250 and/or the program memories 246 as semiconductor memories, magnetically readable memories, and/or optically readable memories, for example.

The one or more processors 248 may be adapted and configured to execute any one or more of the plurality of software applications 264 and/or any one or more of the plurality of software routines 268 residing in the program memory 246, in addition to other software applications. One of the plurality of applications 264 may be a client application 266 that may be implemented as a series of machine-readable instructions for performing the various tasks associated with receiving information at, displaying information on, and/or transmitting information from the laptop computer 114.

One of the plurality of applications 264 may be a native application and/or web browser 270, such as Apple's Safari®, Google Chrome™, Microsoft Internet Explorer®, and Mozilla Firefox® that may be implemented as a series of machine-readable instructions for receiving, interpreting, and/or displaying web page information from the chromatin interaction server 102 while also receiving inputs from a user such as a health care professional or a researcher. Another application of the plurality of applications may include an embedded web browser 276 that may be implemented as a series of machine-readable instructions for receiving, interpreting, and/or displaying web page information from the chromatin interaction server 102.

One of the plurality of routines may include a spatial organization display routine 272 which obtains indications of bin pairs and indication of normalized interaction frequencies and presents a spatial interaction map on the display 240. Another routine in the plurality of routines may include a data entry routine 274 which obtains a set of read pairs, a set of bins, or a selection of two sets of bins to include as axes in a squared genome matrix, and transmits the set of read pairs, set of bins, or selection of two sets of bins to the chromatin interaction server 102.

Preferably, a user may launch the client application 266 from a client device, such as one of the client devices 106-116 to communicate with the chromatin interaction server 102 to implement the chromatin interaction system 100. Additionally, the user may also launch or instantiate any other suitable user interface application (e.g., the native application or web browser 270, or any other one of the plurality of software applications 264) to access the chromatin interaction server 102 to realize the chromatin interaction system 100.

As mentioned above, the chromatin interaction server 102 as shown in FIG. 1A may include a memory 150 which may store instructions executable on the processors 142 for a spatial organization module 160.

Figure 2:
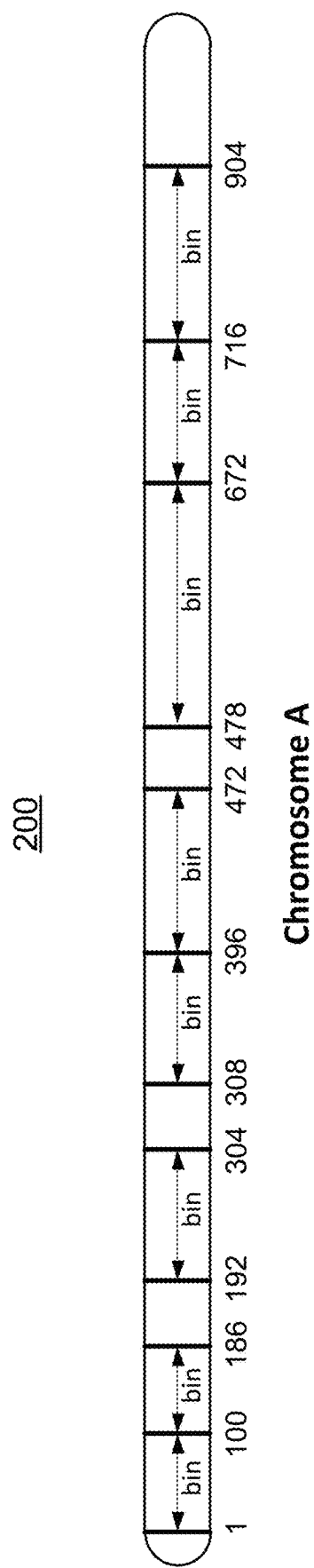
FIG. 2 depicts an example set of bins each corresponding to a contiguous segment of loci in a chromosome in accordance with the presently described embodiments.

FIG. 2 illustrates an example set of bins 200 each representing a contiguous segment of a chromosome illustratively labeled Chromosome A. In this example, each bin includes several loci within Chromosome A. A first bin is from locus 1 to locus 100, a second bin is from locus 100 to locus 186, a third bin is from locus 192 to locus 304, a fourth bin is from locus 308 to locus 396, a fifth bin is from locus 396 to locus 472, a sixth bin is from locus 478 to locus 672, a seventh bin is from locus 672 to locus 716, and an eighth bin is from locus 716 to locus 904. Each bin may represent a different cutsite increment or functional element within Chromosome A, such as a gene, TAD, chromatin state segment, loop domain, chromatin domain, etc. In the example set, the bins are non-overlapping and the size of each bin (or length of the chromosome segment for each bin) varies. As mentioned above, the bins may be selected by a health care professional or researcher, may be determined from previous studies, may be pre-stored bins in the database 154, or may be selected in any suitable manner. While the example set of bins 200 are within Chromosome A, bins may be generated across the entire genome or any suitable portion thereof and may be any suitable sizes.

As described above, the chromatin interaction server 102 and more specifically, the spatial organization module 160 may obtain two sets of bins, similar to the set of bins 200 and may generate a squared genome matrix where each set of bins is an axis of the matrix. In some embodiments, both sets of bins are the same and correspond to the same chromosomes or other genomic regions. In other embodiments, both sets of bins correspond to the same chromosomes or genomic regions but the bins are different, i.e., the chromosomes or genomic regions are segmented differently for each axis. In yet other embodiments, the two sets of bins correspond to different chromosomes or other genomic regions. In any event, the sets of bins to be used as axes in the matrix may be selected by a health care professional or researcher via a client device 106-116 or may be selected in any suitable manner.

While the bin sets have been described above with reference to chromosomes (e.g., a set of bins corresponding to Chromosome A), this is merely one example for ease of illustration only. A bin set may be correspond to any suitable set of segments of DNA sequence within the genome of a human or other organism, such as a genome-wide collection of TADs, a genome-wide collection of genes, a genome-wide collection of chromatin state segments, a collection of loci of interest in a particular biomedical context, etc. In addition to genome-wide collections, a bin set may be allele-specific, and may correspond to a particular haplotype and/or diplotype. Furthermore, multiple bin sets may be generated depending upon the ploidy level and/or copy number. More generally, a bin set may include any collection of bins, where each of the bins correspond to the same type of functional element (e.g., a set of TADs, genes, chromatin state segments, loci, loop domains, chromatin domains, etc.). For example, bin sets may be selected for a genome-wide search for long range interactions, a focused search for the interaction partners of a particular locus or set of loci, a genome-wide mapping of regulatory circuits, comprehensive evaluation of inter-cell-type variability in long range interactions, Hi-C based diagnostic and prognostic biomarkers, etc. However, bin sets do not necessarily have to correspond to the same type of functional element and may include any suitable set of bins.

Figure 3:
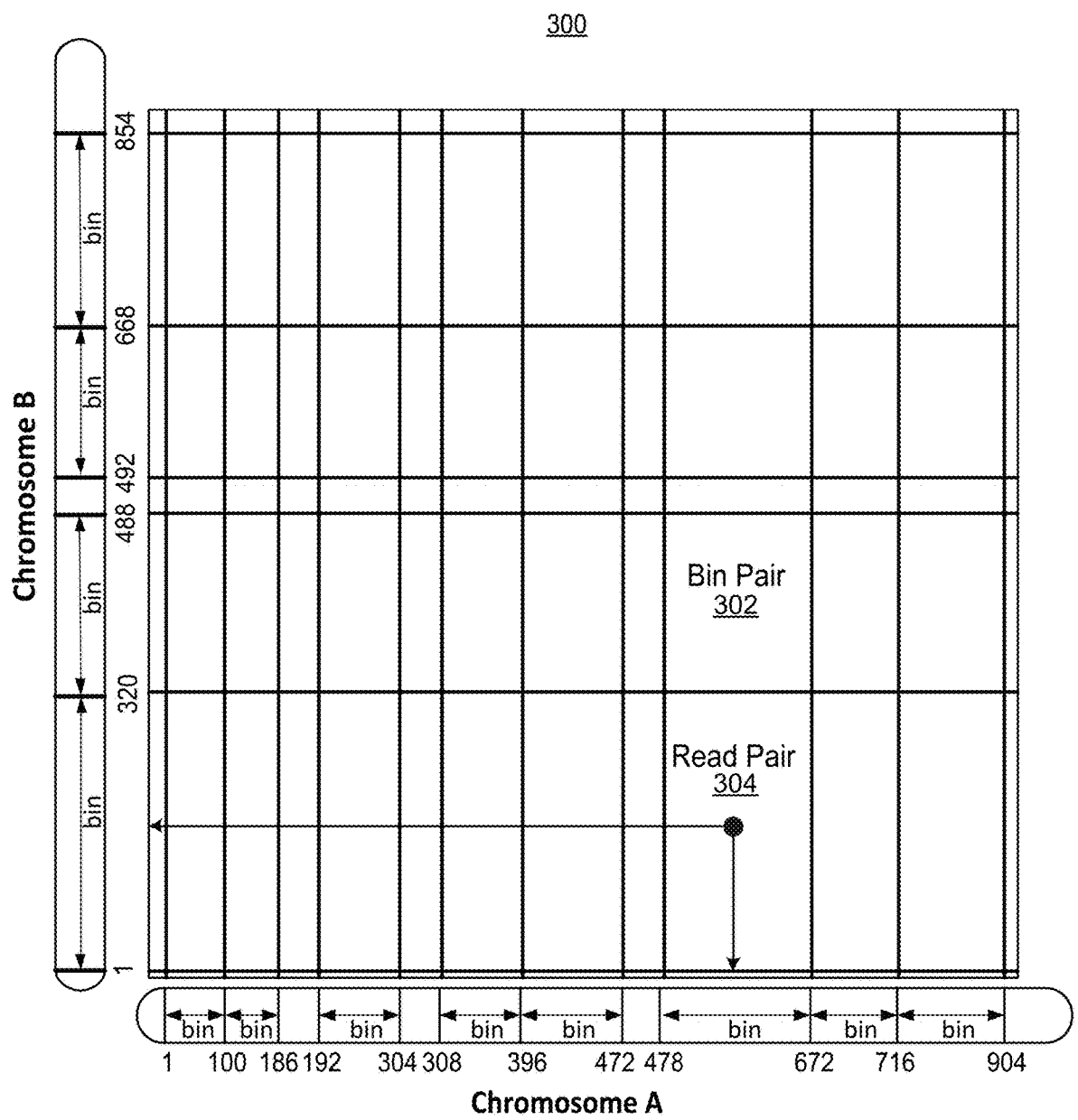
FIG. 3 depicts an example squared genome matrix of bin pairs in accordance with the presently described embodiments.

FIG. 3 illustrates an example squared genome matrix of bin pairs 300 which may be generated by the chromatin interaction server 102 and more specifically, the spatial organization module 160. In this example, a set of bins from Chromosome A may correspond to one axis of the matrix and a set of bins from Chromosome B may correspond to the other axis. The rectangular regions of the matrix corresponding to a bin from one axis and a bin from the other axis may be referred to as bin pairs. For example, bin pair 302 corresponds to ChrA:478-672*ChrB:320-488. As illustrated in example squared genome matrix, the bin pairs are different shapes and sizes. Some bin pairs are rectangular while others more closely resemble a square (e.g., bin pair 302). Additionally, the rectangular areas for the bin pairs differ within the matrix.

In addition to generating the matrix, the chromatin interaction server 102 identifies read pairs within each bin pair. A set of read pairs may be obtained from the database 154, may be provided by the researcher or health care professional via the client device 106-116, or may be obtained in any suitable manner. In any event, a read pair may be identified within a bin pair when both reads are within the rectangular area occupied by the bin pair. For example, the rectangular area occupied by the bin pair that contains read pair 304 spans from ChrA:478-672*ChrB:1-320. This means that any read pair having a Chromosome A locus between 478 and 672 and a Chromosome B locus between 1 and 320 is within the bin pair. Read pair 304 may include the loci ChrA:570, ChrB:160 which is within the rectangular area of ChrA:478-672*ChrB:1-320. In some embodiments, read pairs may be matched to bin pairs using a binary search tree, another type of search tree such as a quad tree, k-d tree or B-tree, or any other suitable data structure for efficient searching, such as a hash table.

The chromatin interaction server 102 may then identify a subset of read pairs corresponding to each bin pair. For each bin pair, the corresponding subset of read pairs may be used to determine the actual density of read pairs for the bin pair or interaction frequency. In some embodiments, the actual density of read pairs for the bin pair may be the number of read pairs within the bin pair or the number of read pairs divided by the rectangular area occupied by the bin pair. In any event, the interaction frequencies for each bin par may be normalized according to a density function.

Figure 4:
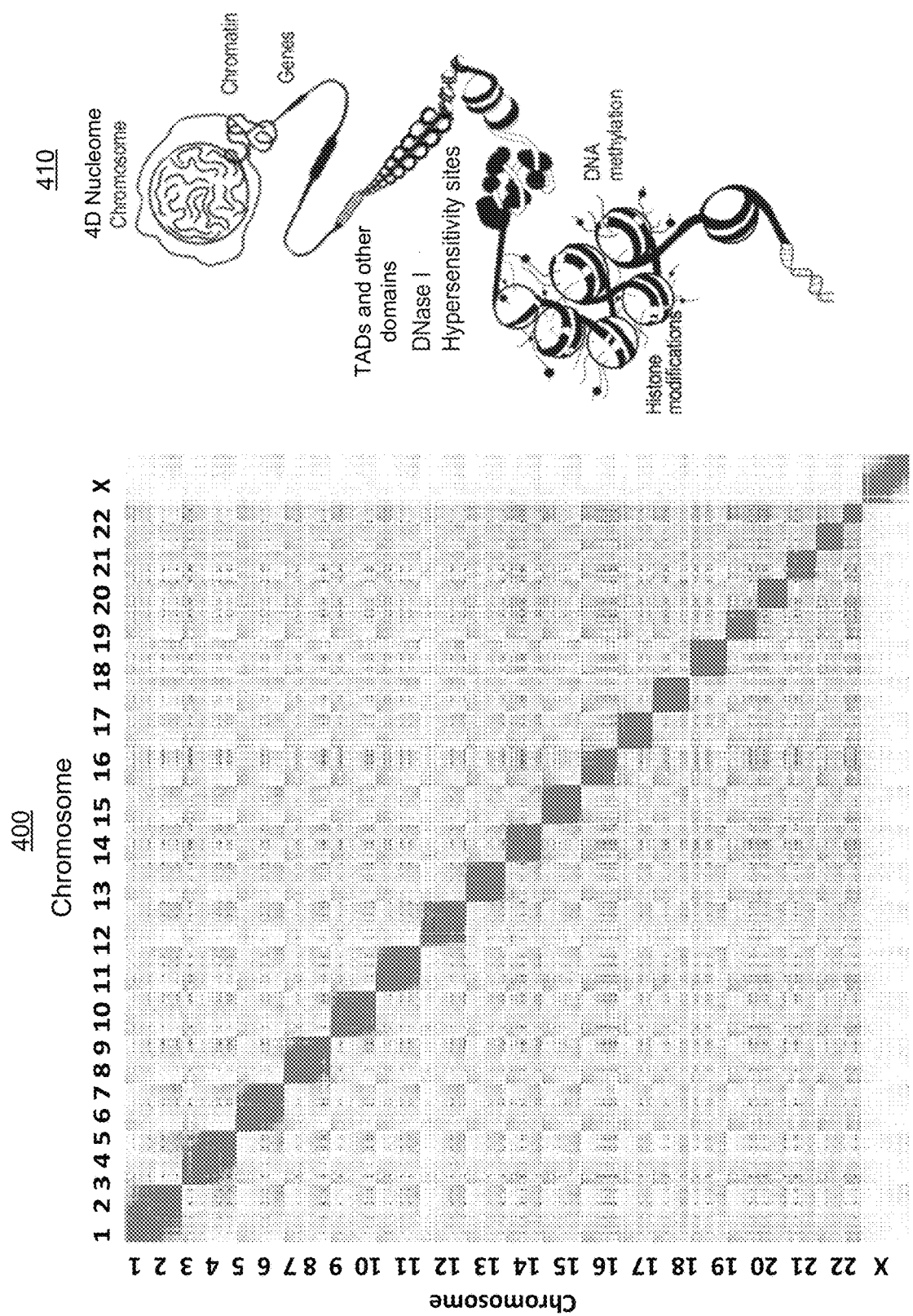
FIG. 4 depicts an example spatial interaction map of bin pairs and respective normalized interaction frequencies in accordance with the presently described embodiments.

In some embodiments, the chromatin interaction server 102, and more specifically, the spatial organization module 160 may provide indications of the bin pairs and indication of the normalized interaction frequencies to a researcher's or health care professional's client device 106. The client device 106 may display a graphical representation of the bin pairs and normalized interaction frequencies. FIG. 4 illustrates an example spatial interaction map 400 or heat map of bin pairs and respective normalized interaction frequencies, which may be presented on the client device 106. The bin sets illustrated in FIG. 4 represent the human genome (chromosomes 1-22, X). In the example spatial interaction map 400, normalized interaction frequencies for bin pairs are represented with gradations of color to produce a two dimensional map of chromatin organization. More specifically, bin pairs having larger normalized interaction frequencies are highlighted in darker colors. The spatial interaction map 400 may resemble the squared genome matrix as described above with reference to FIG. 3 in graphical form. As shown in FIG. 4, the bin pairs along a diagonal line from top left to bottom right on the spatial interaction map 400 are presented with darker colors than the other bin pairs in the spatial interaction map 400. Accordingly, these bin pairs may have enriched contacts. In addition, the contacts in the squares along the axis representing intrachromosomal contacts are darker than those in the off-axis interchromosomal regions of squared genome space. In general, intrachromosomal "cis" regions have higher contact frequencies than interchromosomal "trans" regions. The collection of regions with enriched and depleted contacts and the degree of contact may be assessed for many useful purposes in respective embodiments.

The spatial interaction map 400 and/or other representations of such contacts may be used to generate 3D and 4D chromatin structures, such as the 3D chromatin structure 410. The 3D chromatin structure 410 depicts a 4D nucleome with chromosomes located in chromatin-bound territories in the nucleus. Euchromatin is characterized by DNase 1 hypersensitivity, and specific combination of histone marks that define active genomic regulatory elements. For example, promoters may commonly bear the marks H3K4me3 and H3K27ac, and enhancers may commonly bear the marks H3K4me1 and H3K27ac. An enhancer can either increase or decrease transcription in its target genes, which may be sequence proximal, and/or spatially localized (via, e.g., the methods described above) and/or functionally connected (via, e.g., molecular QTL connection) to the enhancer, either singly or in combination. Heterochromatin is localized to the interior of chromosome territories and the periphery of the nucleus, near the nuclear lamin and the nucleolus, and is characterized by its own pattern of repressive chromatin marks and DNA bound proteins, as well as spatial compaction and linker histones. Recent research demonstrates that, in the brain, the DNA sequence CAC is a common site of methylation, in contrast to other tissues where CpG is most often methylated. Additionally, in the brain, 5-hydroxymethylcytosine (5hmC), a reactive species carrying a distinct element of epigenomic information, is relatively common. In contrast, in the periphery, methylcytosine (hmC) is common.

Figure 5:
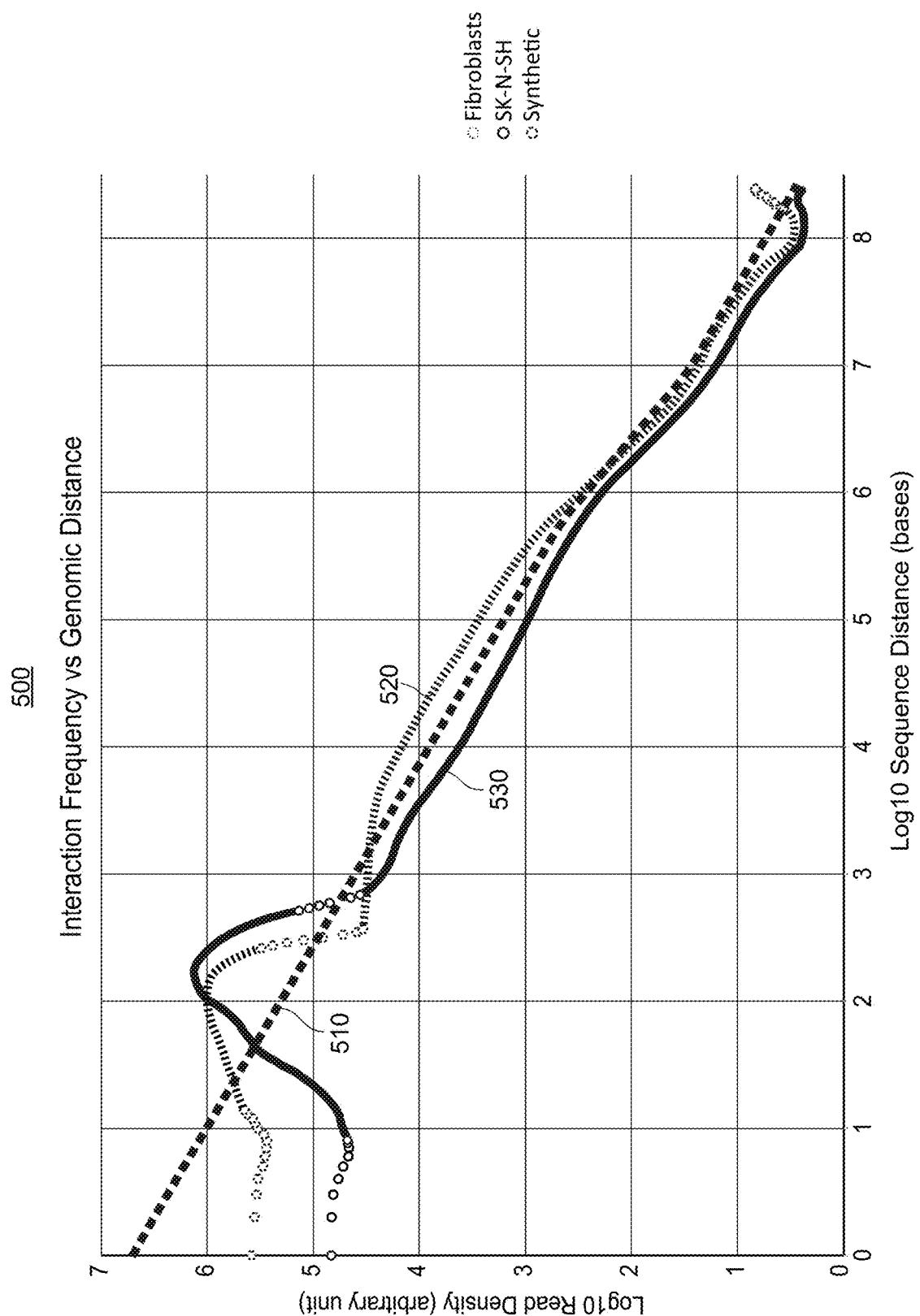
FIG. 5 depicts an example density functions each representing the density of pairwise contacts as a function of genomic distance in accordance with the presently described embodiments.

As mentioned above, to determine normalized interaction frequencies, the spatial organization module 160 may apply a density function to the bin pairs to calculate an expected density for each bin pair. FIG. 5 illustrates an example graph 500 depicting three example density functions 510, 520, 530 each representing the real or ideal density of read pairs as a function of genomic distance across all of the read pairs in the set. As shown in the example graph 500, each of the density functions 510-530 varies in a generally downward-sloping manner as a function of genomic distance as a larger number of read pairs include reads within close proximity of each other. The density function 510 monotonically decreases, while density functions 520 and 530 increase at first as a function of distance and then decrease, with variable slope and level at each distance position. The density function 510 is a synthetic function based on a published power law spline model, a synthetic distance density curve of the type sometimes used to normalize Hi-C datasets, while the other two density functions 520, 530 are empirical density functions. The density function 520 is based on a dataset from SK—N—SH cells (neuronal cells) and the density function 530 is based on a dataset from fibroblasts (skin cells). However, these are merely a few example density functions for a few sets of read pairs. The density as a function of genomic distance may exhibit other patterns for other sets of read pairs (e.g., the function may decay at faster or slower rates as the genomic distance increases). Such a function may be generated empirically for a particular database of sequence contacts and suitably adjusted.

In any event, the chromatin interaction server and more specifically, the spatial organization module 160 may apply one of the density functions 510-530 illustrated in the example graph 500 to calculate an expected density for each bin pair. In some embodiments, the spatial organization module 160 may select an empirical density function applicable to the selected bin pairs. For example, when the bin sets include bins representing segments of DNA sequence expressed in skin cells, the spatial organization module 160 may select the density function 530 based on the dataset from fibroblasts. When the bin sets include bins representing segments of DNA sequence expressed in neurons, the spatial organization module 160 may select the density function 520 based on the dataset from SK—N—SH cells. In other embodiments, the spatial organization module 160 may select the synthetic density function 510.

For a particular bin pair, the spatial organization module 160 may integrate the selected density function (e.g., density function 520) across the rectangular area occupied by the bin pair to determine the expected density for the bin pair. Then for each bin pair, the spatial organization module 160 may compare the expected density for the bin pair to the actual density using various statistical methods to determine whether the expected density differs from the actual density by a statistically significant amount. For example, the null hypothesis may be that the actual density is not greater than the expected density for the bin pair. The spatial organization module 160 may compare the expected density to the actual density according to a Poisson distribution or any other suitable distribution using a one-tailed test to generate a p-value. When the p-value is less than a threshold confidence level (e.g., a p-value of 0.05 corresponds to 95% confidence, a p-value of 0.01 corresponds to 99% confidence, etc.), the null hypothesis may be rejected and the spatial organization module 160 may determine that the bin pair includes enriched contacts. In some embodiments, the spatial organization module 160 may apply false discovery rates to the p-values, such as Benjamini false discovery rates, or other statistical methods for multiple comparison control.

In another example, the null hypothesis may be that the actual density is not less than the expected density for the bin pair. The spatial organization module 160 may compare the expected density to the actual density according to a Poisson distribution or any other suitable distribution using a one-tailed test to generate a p-value. When the p-value is less than a threshold confidence level (e.g., a p-value of 0.05 corresponds to 95% confidence, a p-value of 0.01 corresponds to 99% confidence, etc.), the null hypothesis may be rejected and the spatial organization module 160 may determine that the bin pair includes depleted contacts. In some embodiments, the spatial organization module 160 may apply false discovery rates to the p-values, such as Benjamini false discovery rates, or other statistical methods for multiple comparison control.

In yet another example, the null hypothesis may be that the actual density is the same as the expected density for the bin pair. The spatial organization module 160 may compare the expected density to the actual density according to a Poisson distribution or any other suitable distribution using a two-tailed test to generate a p-value. When the p-value is less than a threshold confidence level (e.g., a p-value of 0.05 corresponds to 95% confidence, a p-value of 0.01 corresponds to 99% confidence, etc.), the null hypothesis may be rejected and the spatial organization module 160 may determine that the bin pair includes differential or aberrant contacts (i.e., enriched or depleted contacts). In some embodiments, the spatial organization module 160 may apply false discovery rates to the p-values, such as Benjamini false discovery rates, or other statistical methods for multiple comparison control.

While the statistical analyses are described herein with reference to a Poisson distribution, this is merely one type of statistical test that may be used to determine whether there is a statistically significant difference between the actual density and expected density of a bin pair. Other statistical tests may include a T-test, a chi-squared test, a G-test, a regression test, etc. Furthermore, machine learning methods may also be used in addition to statistical tests, including, but not limited to regression algorithms (e.g., ordinary least squares regression, linear regression, logistic regression, stepwise regression, multivariate adaptive regression splines, locally estimated scatterplot smoothing, etc.), instance-based algorithms (e.g., k-nearest neighbors, learning vector quantization, self-organizing map, locally weighted learning, etc.), regularization algorithms (e.g., Ridge regression, least absolute shrinkage and selection operator, elastic net, least-angle regression, etc.), decision tree algorithms (e.g., classification and regression tree, iterative dichotomizer 3, C4.5, C5, chi-squared automatic interaction detection, decision stump, M5, conditional decision trees, etc.), clustering algorithms (e.g., k-means, k-medians, expectation maximization, hierarchical clustering, spectral clustering, mean-shift, density-based spatial clustering of applications with noise, ordering points to identify the clustering structure, etc.), association rule learning algorithms (e.g., apriori algorithm, Eclat algorithm, etc.), Bayesian algorithms (e.g., naïve Bayes, Gaussian naïve Bayes, multinomial naïve Bayes, averaged one-dependence estimators, Bayesian belief network, Bayesian network, etc.), artificial neural networks (e.g., perceptron, Hopfield network, radial basis function network, etc.), deep learning algorithms (e.g., multilayer perceptron, deep Boltzmann machine, deep belief network, convolutional neural network, stacked autoencoder, generative adversarial network, etc.), dimensionality reduction algorithms (e.g., principal component analysis, principal component regression, partial least squares regression, Sammon mapping, multidimensional scaling, projection pursuit, linear discriminant analysis, mixture discriminant analysis, quadratic discriminant analysis, flexible discriminant analysis, factor analysis, independent component analysis, non-negative matrix factorization, t-distributed stochastic neighbor embedding, etc.), ensemble algorithms (e.g., boosting, bootstrapped aggregation, AdaBoost, stacked generalization, gradient boosting machines, gradient boosted regression trees, random decision forests, etc.), reinforcement learning (e.g., temporal difference learning, Q-learning, learning automata, State-Action-Reward-State-Action, etc.), support vector machines, mixture models, evolutionary algorithms, probabilistic graphical models, etc.

Additionally, while the methods described herein utilize false discovery rates for multiple comparison control, any suitable multiple comparison control methods may be applied to the p-values, such as a false coverage rate, a Bayesian approach, etc.

The bin pairs having enriched or depleted contacts may then be used for predicting molecular phenotypes for a subject based on the spatial interactions of loci within their respective genomes. The enriched or depleted contacts may also be used to model 3D and 4D structures of chromosomes, and to identify altered TAD boundaries and spatial interactions in a tissue sample for determining genetic disease or oncology. Moreover, the enriched or depleted contacts may be used for determining whether and/or to what extent a pair of loci interact with each other in a particular tissue or cell line. Still further, enriched or depleted contacts may be used to identify ploidy and translocations based on aberrant contacts and/or total contact density in squared genome space.

For example, a health care professional may obtain a biological sample for measuring a subject's chromatin interaction data (e.g., from a cheek swab, a skin sample, a biopsy, a blood sample, lymph fluid, bone marrow, cell lines, tissues, model organisms, etc.) and provide laboratory results obtained by analyzing the biological sample to the chromatin interaction server.

Figure 6:
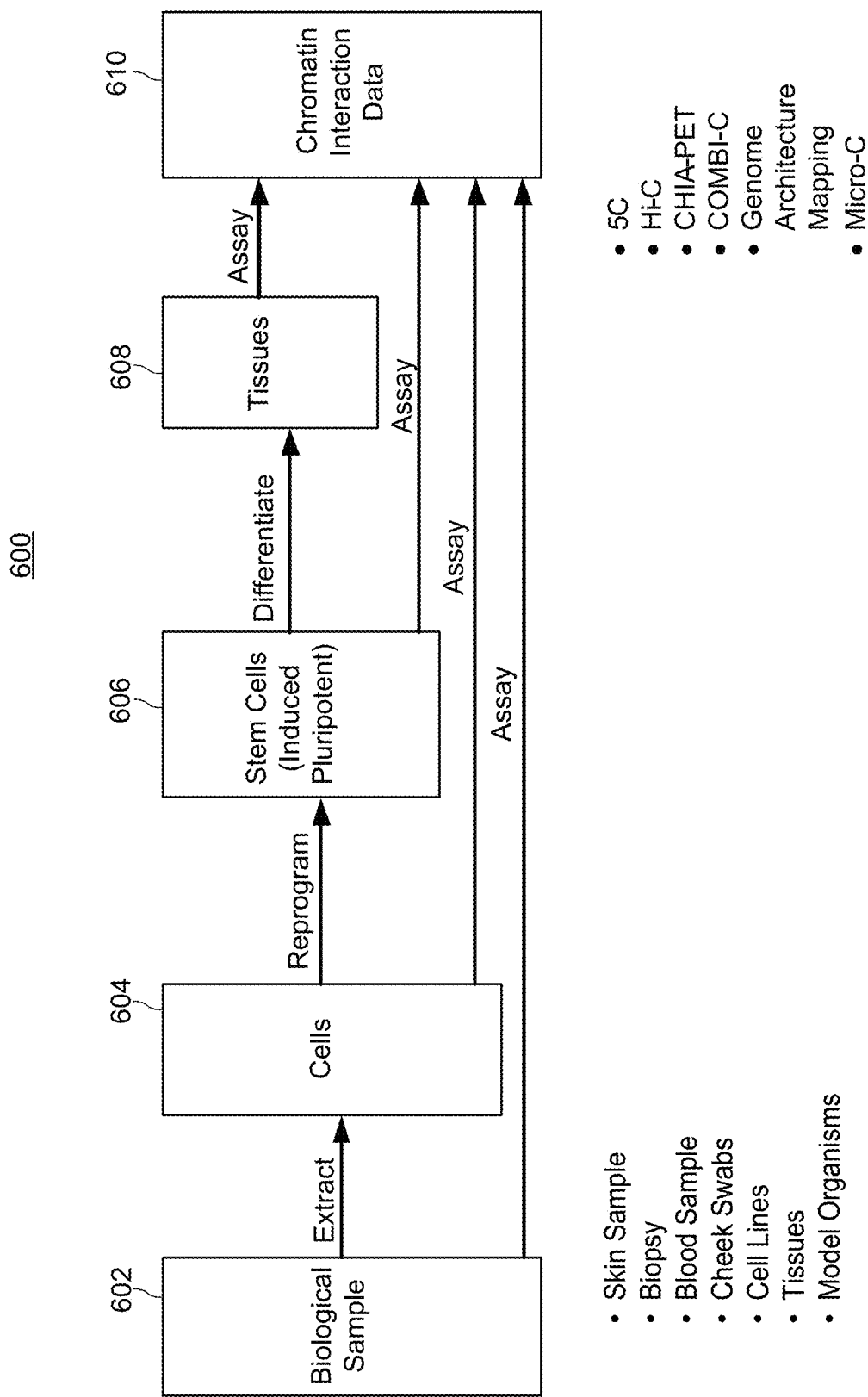
FIG. 6 is a block diagram representing an exemplary process for generating chromatin interaction data from subjects' biological samples.

An example process 600 for generating chromatin interaction data from a subject's biological sample is illustrated in FIG. 6. The process may be performed by an assay laboratory or other suitable organization. At block 602, a subject's biological sample is obtained by a health care professional and sent to an assay laboratory for analysis. The biological sample may include the subject's skin, blood, lymph fluid, bone marrow, cheek cells, cell lines, tissues, etc. Cells are then extracted from the biological sample at block 604 and reprogrammed into stem cells at block 606, such as induced pluripotent stem cells (iPSCs). Then at block 608, the iPSCs are differentiated into various tissues, such as neurons, cadiomyoctyes, etc., and assayed to obtain chromatin interaction data at block 610. The chromatin interaction data may include 5C data, Hi-C data, ChIA-PET data, Combi-C data, Genome Architecture Mapping data, Micro-C data, etc.

Moreover, individual loci of DNA sequence may be identified as associated with or causatively associated with a particular molecular phenotype. A set of bins may also be identified containing the individual loci. Then, when a subject's chromatin interaction data is analyzed with respect to a particular molecular phenotype or set of molecular phenotypes (e.g., molecular phenotypes indicative of a response to valproic acid), the iPSCs may be assayed for the loci associated with or causatively associated with the particular set of molecular phenotypes. The bin sets corresponding to the loci identified from the assay may be compared to contact data from such bin sets in other bio-cellular systems, e.g., such systems might constitute two different tissues within the human body, tissue samples from two different individuals, a cell line subjected to a medical treatment as versus a control sample, or multiple cell cycle conditions or cellular differentiation states for the same tissue, cell line, or organism. Then, the chromatin interaction server 102 may predict molecular phenotypes for the subject based on the comparison. For example, if the subject's iPSCs include a read pair within a bin set having loci that are associated with or causatively associated with a particular response to valproic acid, the chromatin interaction server 102 may predict that the subject will have the particular response to valproic acid.

More generally, the selection of which chromatin interaction data to assay may be based on chromatin interaction data identified as being associated with or causally associated with the set of molecular phenotypes under examination for the subject.

More specifically, cells are reprogrammed into iPSCs through the introduction of transcription factors or "reprogramming factors" or other agents into a given cell type. For example, the Yamanaka factors including the transcription factors Oct4 (POU5F1), Sox2 (SOX2), cMyc (MYC), and Klf4 (KLF4) may be used to reprogram cell into iPSCs. The iPSCs may then be differentiated into a variety of tissues, such as neurons, adipocytes, cardiomyocytes, pancreatic beta-cells, etc. After the iPSCs have been differentiated, the differentiated iPSCs may be assayed using various assaying techniques such as DNA methylation analysis, DNase footprinting assay, filter binding assay, etc. to identify epigenomic information. In effect, the system performs a virtual biopsy and the differentiated iPSCs take on the phenotypic and epigenomic properties of their corresponding tissues at least to some extent.

In the embodiments described above, cells are extracted from the subject's biological sample, reprogrammed into stem cells, differentiated into various tissues, and assayed to obtain chromatin interaction data (assay on differentiated, reprogrammed cells). Alternatively, in some embodiments, the subject's biological sample is assayed without extracting cells (cell-free assay). In other embodiments, cells are extracted from the subject's biological sample and assayed without being reprogrammed or differentiated (assay on primary cells). In yet other embodiments, the cells are reprogrammed into iPSCs and assayed without being differentiated (assay on reprogrammed stem cells). For example, the iPSCs may be assayed without being differentiated to obtain stem cell omics. While these are merely a few example processes for generating chromatin interaction data from a subject's biological sample, assays may be performed at any suitable stage in the process and chromatin interaction data may be generated in any suitable manner.

In some embodiments, the spatial organization module 160 may then provide indications of the bin pairs and indication of the normalized interaction frequencies to a researcher's or health care professional's client device 106. FIG. 7A illustrates an example display 700 of enriched contacts and corresponding loci as well as SNPs associated with molecular phenotypes, which may be presented on the client device 106. The example display 700 includes the TADs (each made up of a set of individual loci of DNA sequence) which contain a collection of regulatory SNPs considered significant in response phenotypes for two drugs that induce neurogenesis in adult humans, specifically valproic acid and ketamine. As an exemplary instance of an embodiment for the present invention, scientists investigating these drugs may wish to discern the mechanisms by which they function. They may wish to identify the target genes of these regulatory SNPs, and therefore to find the spatial contact partners of the TADs that contain them, in a system of interest. They may also wish to find out which of these TADs contact each other in a system of interest. In other embodiments, a collection of loci of interest may be identified corresponding to a collection of variants for a drug, disease, or other molecular phenotype, or a collection of loci of interest for a particular subject, etc.

The example display 700 includes the chromosome (e.g., chromosome 17), loci (e.g., 33720000-35360000), TAD (e.g., 1977), candidate contacts (e.g., 1), and target gene (e.g., CCL2) associated with a bin pair having enriched contacts. Each TAD in the display 700 exhibits some distal contacts ranging from three (e.g., TAD 1977) up to several hundred (e.g., TAD 2112) throughout the genome. TADs containing pharmacokinetic loci, e.g., the CYP genes which metabolize these drugs, appear to harbor the largest number of contacts. The display 700 also includes the SNPs (e.g., rs2857654) associated with the enriched contacts and a drug (e.g., valproate) in which its response is correlated with the SNP. In this manner, the health care professional or researcher may view the SNPs associated with enriched contacts and their corresponding molecular phenotypes. However, this is merely one example display of numeric indications of the bin pairs, for ease of illustration only. In other embodiments, the client device 106 may display a numeric indication of each bin pair (e.g., Chr11:8560000-10720000*Chr11:4580000-4780000), a numeric indication of the interaction frequencies for the bin pairs such as p-values, an indication of whether the bin pair has enriched contacts, etc.

Figure 7B:
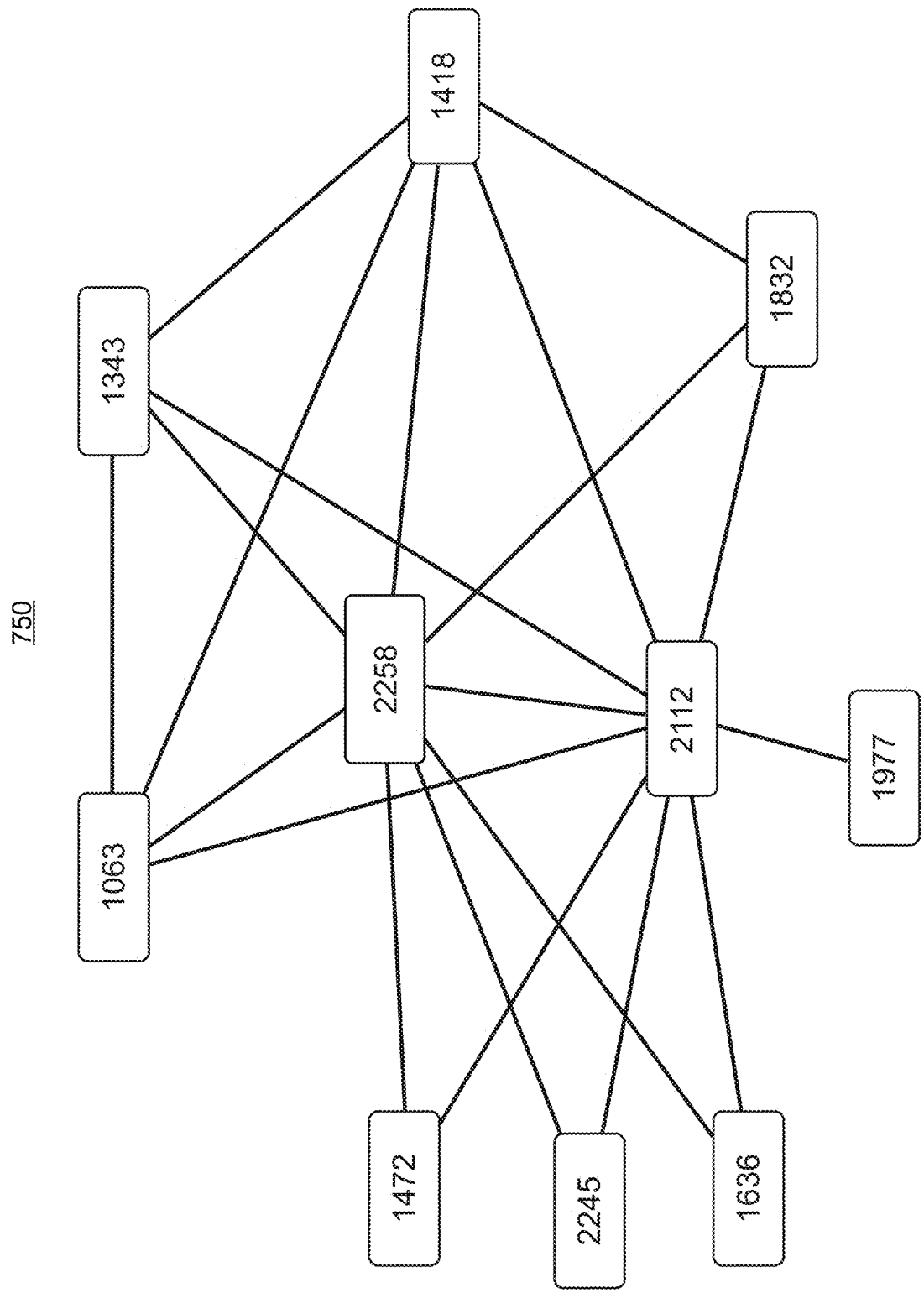
FIG. 7B depicts an example chromatin interaction network generated from the spatial interaction data in accordance with the presently described embodiments.

In yet other embodiments, the client device 106 may display a chromatin interaction network generated from the spatial contact data. FIG. 7B illustrates an example display of a chromatin interaction network 750 generated from the spatial contact data described with reference to FIG. 7A. In some embodiments, the chromatin interaction network 750 may be presented on the client device 106. In any event, TADs with at least one candidate contact, as illustrated in the display 700, are included in the chromatin interaction network 750. For example, TAD 1977 one candidate contact and accordingly is included in the chromatin interaction network 750. Furthermore, TAD 1977 is connected with its candidate contact (TAD 2112). Moreover, TAD 2245 is connected with TADs 2258 and 2112, and TADs 1567, 1862, and 693 have zero candidate contacts, and thus are not included in the chromatin interaction network 750. Therefore, of the 13 identified TADs shown in the display in FIG. 7A, 10 include connections to other TADs within the set forming a densely interacting spatial network of functionally related TADs. In any event, TAD 1636 is connected with TADs 2258 and 2112, and TAD 1832 is connected with TADs 2258, 2112, and 1418. Still further, TAD 2112 is connected with every other TAD in the chromatin interaction network 750, and TAD 2258 is connected with every other TAD in the chromatin interaction network 750 besides for TAD 1977. Additionally, TAD 1063 is connected with its four candidate contacts (TADs 2112, 2258, 1418, and 1343). TAD 1343 also has four candidate contacts and is connected with each of them (TADs 2245, 1063, 2258, 1343, and 1418) in the chromatin interaction network 750. TAD 1418 is connected with TADs 1832, 2112, 2258, 1063, and 1343 in the chromatin interaction network 750, and TAD 1472 is connected with TADs 2258 and 2112. None of the TADs included in the chromatin interaction network 750 were identified by alternative systems, such as HOMER described in more detail below. TADs 1064, 2258, 2112, and 1418 are pharmacokinetic TADs while TADs 1472, 2245, 1636, 1977, 1343, and 1832 are pharmacodynamics TADs.

In this manner, a health care professional or researcher viewing the chromatin interaction network 750 on the client device 106 may see the strength of the relationships within the chromatin interaction network 750. For example, the health care professional or researcher may see that TAD 2112 has a relationships with every other TAD in the chromatin interaction network 750, while TAD 1977 is a part of the chromatin interaction network 750, but only has a relationship with one TAD. In light of the distinct set of genes and variants present in each TAD, and their distinct biological functions and significance in various biomedical and research contacts, the accurate detection and display of chromatin contacts may serve many useful purposes in various embodiments.

Figure 9:
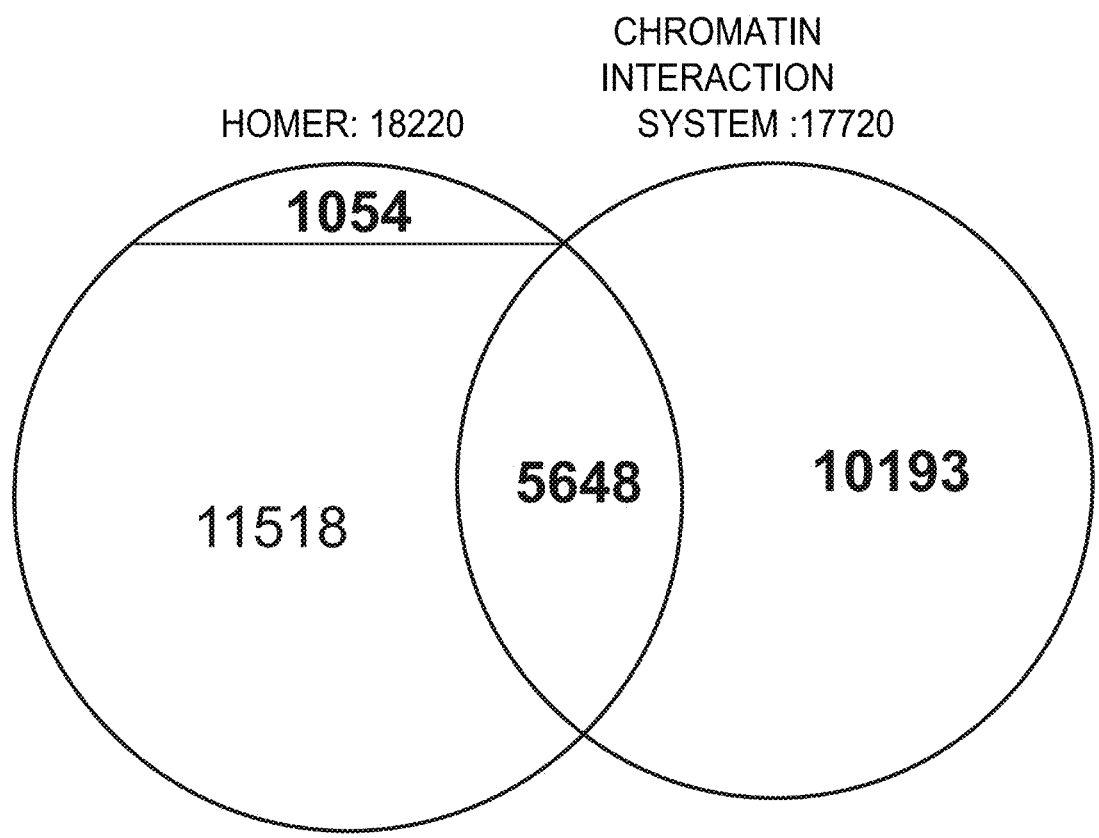
FIG. 9 illustrates a Venn diagram depicting a comparison of the number of contacts identified by the chromatin interaction system and the number of contacts identified by an alternative system.

FIG. 9 illustrates the results of a comparison between the chromatin interaction system and HOMER, a widely used Hi-C compiler. The chromatin interaction system and HOMER analyzed a dataset of human fibroblasts, where the chromatin interaction system generated a matrix of TAD bins on both axes. For HOMER, fixed bins having a 1 Mb resolution were used. As shown in FIG. 9, HOMER detected 18,220 contacts while the chromatin interaction system detected 17,720 contacts and both systems detected the same 5,648 contacts. The chromatin interaction system detected 10,193 contacts which were not detected by HOMER. Therefore, the chromatin interaction system identified contacts which were not detected by previous systems due to the improved discerning power of the chromatin interaction system. Accordingly, the chromatin interaction system identifies more long range contacts (e.g., cis interactions at a range of greater than 10 Mb which were enriched twofold or more and passed comparison control, squared genome wide) than previous systems.

HOMER detected 12,572 contacts which were not detected by the chromatin interaction system. However, among these contacts 82% fail the fold-change cutoff in the chromatin interaction system, 90% fail the FDR cutoff, and 72% fail both cutoffs. Among such pairs, 92% have a neighbor TAD pair which did have a detected contact in the chromatin interaction system. The non-neighbor discordant HOMER contacts included 1,054 contacts.

Figure 8:
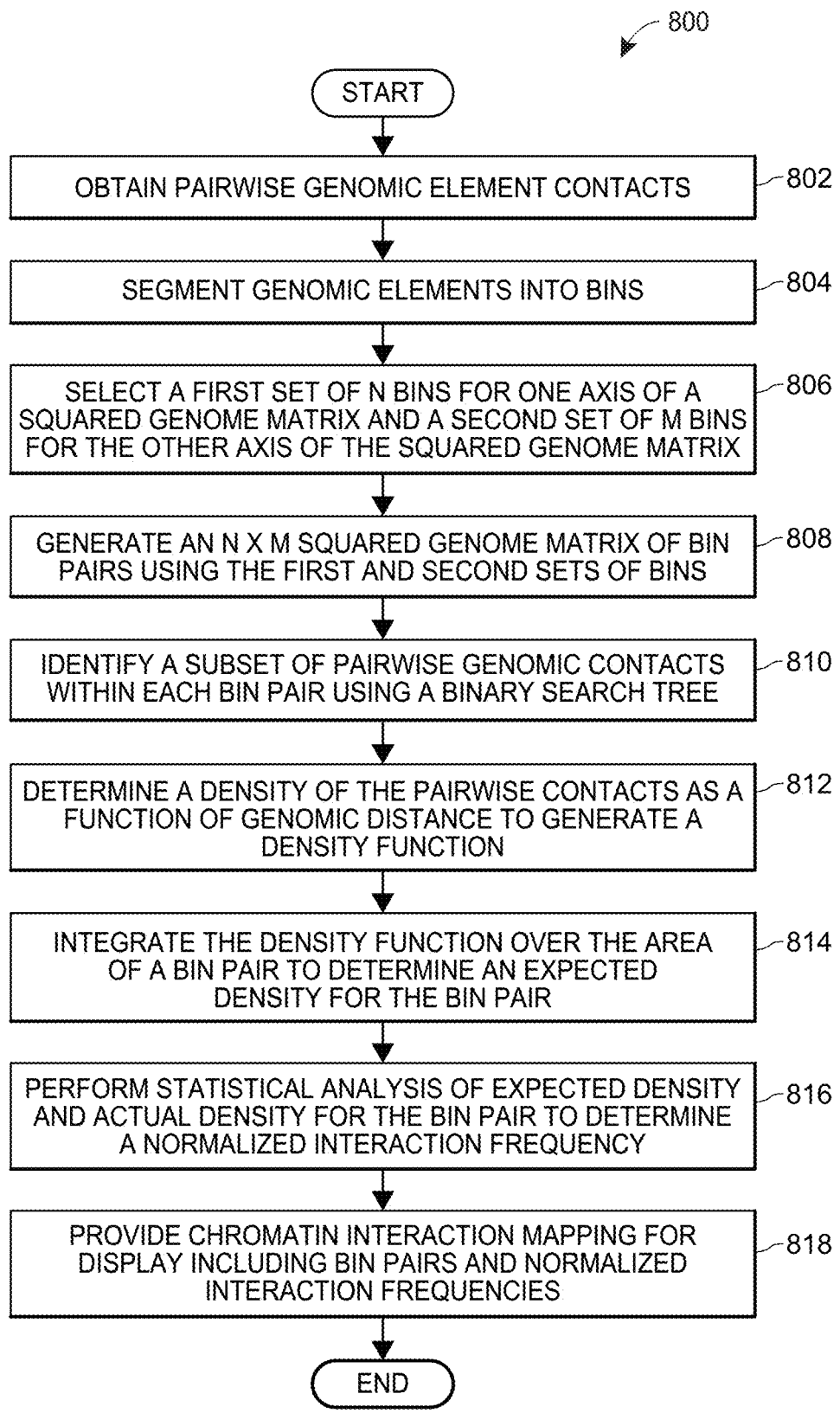
FIG. 8 illustrates a flow diagram representing an exemplary method for analyzing spatial organization of chromatin in accordance with the presently described embodiments.

FIG. 8 depicts a flow diagram representing an exemplary method 800 for analyzing spatial organization of chromatin. The method 800 may be executed on the chromatin interaction server 102. In some embodiments, the method 800 may be implemented in a set of instructions stored on a non-transitory computer-readable memory and executable on one or more processors on the chromatin interaction server 102. For example, the method 800 may be performed by the spatial organization module 160 of FIG. 1A.

The method may include the steps of alignment, quality control, compiling, integration, statistical testing, and result output. More specifically, at block 802, the spatial organization module 160 may obtain a set of pairwise genomic element contacts or read pairs. The set of read pairs may be obtained from the database 154 as shown in FIG. 1A, from the client device 106 of a researcher or professional, or in any other suitable manner. In some embodiments, the researcher or professional may select a particular set of the read pairs for a particular analysis or study and provide the selected set, via the client device 106, to the chromatin interaction server 102. In another example, the sequencing machine 107 may generate sequence data which is provided to the chromatin interaction server 102. The spatial organization module 160 may then identify a set of read pairs from the sequence data. In yet another example, the sequence database 109 may provide preexisting sequence data generated from for example, published literature, clinical trial, consortia, academia, etc., to the chromatin interaction server 102. Then, the spatial organization module 160 may identify a set of read pairs from the sequence data. In some embodiments, the spatial organization module 160 splits the read pairs into their single-ended components and aligns the single-ended components. Then pairs are selected where both reads in the pair present less than a threshold probability (e.g., 0.05) of misalignment in either read.

The spatial organization module 160 may also segment genomic element contacts or reads into bins (block 804). Each bin may represent a different cutsite increment or functional element within a genome or portion of the genome, such as a gene, TAD, chromatin state segment, loop domain, chromatin domain, etc. The bins are non-overlapping and the bin sizes are non-uniform, i.e., the size of each bin (or length of the genome segment for each bin) varies. In some embodiments, the bins may be selected by a health care professional or researcher, via the client device 106, may be determined from previous studies such as from the sequence database 109, may be pre-stored bins in the database 154, or may be selected in any suitable manner. For example, the researcher or health care professional may select a set of bins where each bin represents a different TAD. In another example, the researcher or health care professional may select a set of bins where each bin represents a different gene.

Then at block 806, a first set of n bins and a second set of m bins are selected, where each set corresponds to an axis of an n×m squared genome matrix. The axes may be selected by a health care professional or researcher via a client device 106-116 or may be selected in any suitable manner. In some embodiments, both sets of bins are the same and correspond to the same chromosome. In other embodiments, both sets of bins correspond to the same chromosome but the bins are different, i.e., the chromosome is segmented differently for each axis. In yet other embodiments, the two sets of bins correspond to different chromosomes. In any event, the spatial organization module 160 may generate a squared genome matrix that includes n×m bin pairs (block 810), where a bin pair is one entry or rectangle in the squared genome matrix (e.g., Chr1:1000-2000*Chr8:10000-20000).

Then, the spatial organization module 160 compiles the read pairs into bin pairs. More specifically, the spatial organization module 160 may identify a subset of read pairs that corresponds to each bin pair using a binary search tree, for example (block 810). A read pair may be identified within a bin pair when both reads are within the rectangular area occupied by the bin pair. For example, the rectangular area occupied by the bin pair that contains read pair 304 as shown in FIG. 3, spans from ChrA:478-672*ChrB:1-320. This means that any read pair having a Chromosome A locus between 478 and 672 and a Chromosome B locus between 1 and 320 is within the bin pair. Read pair 304 may include the loci ChrA:570, ChrB:160 which is within the rectangular area of ChrA:478-672*ChrB:1-320. In some embodiments, read pairs may be matched to bin pairs using another type of search tree such as a quad tree, k-d tree or B-tree, or any other suitable data structure for efficient searching, such as a hash table.

At block 812, the spatial organization module 160 generates a density function based on the density of read pairs as a function of genomic distance across the entire set of read pairs. In some embodiments, the density function may be a monotonically decreasing function. For a particular bin par, the density function is integrated over the rectangular area of the bin par (e.g., ChrA:478-672*ChrB:1-320) to determine an expected density for the bin pair (block 814). Expected densities may be determined for each of the bin pairs.

Then, the spatial organization module 160 may compare the expected density for the particular bin pair to an actual density of the particular bin pair. For example, the actual density may be the number of read pairs included within the particular bin pair. The actual and expected densities may be compared using a statistical analysis to determine whether the difference between the expected density differs from the actual density by a statistically significant amount (the normalized interaction frequency) (block 816). For example, the null hypothesis may be that the actual density is not greater than the expected density for the bin pair. The spatial organization module 160 may compare the expected density to the actual density according to a Poisson distribution or any other suitable distribution to generate a p-value. When the p-value is less than a threshold confidence level (e.g., a p-value of 0.05 corresponds to 95% confidence, a p-value of 0.01 corresponds to 99% confidence, etc.), the null hypothesis may be rejected and the spatial organization module 160 may determine that the bin pair includes enriched contacts. In some embodiments, the spatial organization module 160 may apply false discovery rates to the p-values, such as Benjamini false discovery rates, or other statistical methods for multiple comparison control. In another example, the null hypothesis may be that the actual density is not less than the expected density for the bin pair. When the p-value is less than a threshold confidence level, the null hypothesis may be rejected and the spatial organization module 160 may determine that the bin pair includes depleted contacts.

In some embodiments, actual read counts for multiple sets of contacts, e.g. corresponding to different bio-cellular systems or different physiological conditions, may be analyzed together. E.g., such systems might constitute two different tissues within the human body, tissue samples from two different individuals, a cell line subjected to a medical treatment as versus a control sample, or multiple cell cycle conditions or cellular differentiation states for the same tissue, cell line, or organism. Such an analysis may determine, for example, a set of differential contacts between a pair of sets of contacts, by, e.g., comparing the enriched and depleted contacts from each dataset individually. Differential contacts may also be determined by, e.g., using the multiple sampling distribution of the Poisson or other statistical distribution to generate p-values corresponding to the probability of differential interaction frequencies being observed by chance, which may then be corrected with False Discovery Rate or other methods, as described herein.

At block 818, the spatial organization module 160 may provide indications of the bin pairs an indication of normalized interaction frequencies to the client device 106 of a researcher or health care professional. These indications may include numeric indications of the normalized interaction frequencies, such as p-values, a graphical representation of the bin pairs and normalized interaction frequencies, such as a spatial organization map, a list of the bin pairs having enriched contacts, or any other suitable indications.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA), an application-specific integrated circuit (ASIC), or custom silicon) to perform certain operations. A hardware module may also comprise programmable logic or circuitry (e.g., as encompassed within a general-purpose processor, a graphics processing unit (GPU) or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as providing examples only and does not describe every possible embodiment, as describing every possible embodiment would be impractical, if not impossible. One could implement numerous alternate embodiments, using either current technology or technology developed after the filing date of this application.

The following list of aspects reflects a variety of the embodiments explicitly contemplated by the present application. Those of ordinary skill in the art will readily appreciate that the aspects below are neither limiting of the embodiments disclosed herein, nor exhaustive of all of the embodiments conceivable from the disclosure above, but are instead meant to be exemplary in nature.

1. A computer-implemented method for analyzing spatial and temporal organization of chromatin, the method executed by one or more processors programmed to perform the method, the method comprising: obtaining, at one or more processors, a set of pairwise contacts of genomic elements; segmenting, by the one or more processors, genomic elements into a plurality of bins, wherein bin sizes for the plurality of bins are non-uniform; identifying, by the one or more processors, a first set of the plurality of bins and a second set of the plurality of bins; generating, by the one or more processors, a matrix of n×m bin pairs, wherein n corresponds to the first set of the plurality of bins and m corresponds to the second set of the plurality of bins; identifying, by the one or more processors, a subset of pairwise contacts within each of the bin pairs; determining, by the one or more processors, an interaction frequency for each of the bin pairs; normalizing, by the one or more processors, each of the interaction frequencies to generate a normalized interaction frequency for each bin pair; and providing, by the one or more processors, a mapping of chromatin interactions for display on a user interface, including indications of the bin pairs and respective indications of normalized interaction frequencies.

2. The method according to aspect 1, wherein normalizing each of the interaction frequencies includes: determining, by the one or more processors, a density of the set of pairwise contacts as a function of genomic distance to generate a density function; for each of the plurality of bin pairs: integrating, by the one or more processors, the density function over an area of the bin pair to determine an expected density for the bin pair; comparing, by the one or more processors, the subset of pairwise contacts within the bin pair to the expected density for the bin pair by performing a statistical analysis using a Poisson statistical distribution to determine a likelihood that an amount in which an actual density for the bin pair is greater than the expected density for the bin pair is significantly significant; applying, by the one or more processors, a false discovery rate for multiple comparison control to the determined likelihood to determine an adjusted likelihood; and when the adjusted likelihood is less than a threshold likelihood, determining, by the one or processors, that the bin pair has enriched contacts.

3. The method according to either one of aspect 1 or aspect 2, further comprising: performing, by the one or processors, a statistical analysis using a Poisson distribution to determine a second likelihood that the amount in which the actual density for the bin pair is less than the expected density for the bin pair is significantly significant; applying, by the one or more processors, a false discovery rate for multiple comparison control to the determined second likelihood to determine an adjusted second likelihood; and when the adjusted second likelihood is less than a threshold likelihood, determining, by the one or processors, that the bin pair has depleted contacts.

4. The method according to any one of the preceding aspects, wherein the statistical analysis includes a two-tailed test to determine a third likelihood that the amount in which the actual density for the bin pair differs from the expected density is statistically significant; applying, by the one or more processors, a false discovery rate for multiple comparison control to the determined third likelihood to determine an adjusted third likelihood; and when the adjusted third likelihood is less than a threshold likelihood, determining, by the one or processors, that the bin pair has enriched or depleted contacts.

5. The method according to any one of the preceding aspects, wherein at least some of the pairwise contacts are cis contacts, such that both genomic elements in each of the at least some pairwise contacts correspond to a same chromosome; and wherein at least some of the pairwise contacts are trans contacts, such that both genomic elements in each of the at least some pairwise contacts correspond to different chromosomes.

6. The method according to any one of the preceding aspects, wherein the density function is generated from empirical data and at least a portion of the density function decreases as genomic distance increases.

7. The method according to any one of the preceding aspects, further comprising: identifying, by the one or more processors, individual loci of DNA sequence associated with or causatively associated with one or more molecular phenotypes; identifying, by the one or more processors, a set of bins containing the individual loci; obtaining, by the one or more processors, chromatin interaction data for a subject; comparing, by the one or more processors, the chromatin interaction data for the bins containing the individual loci to contact data on such bins in another bio-cellular system; and predicting, by the one or more processors, molecular phenotypes for the subject based on the comparison.

8. The method according to any one of the preceding aspects, further comprising: generating, by the one or more processors, a 3D or 4D model of chromosome structures based on the mapping of chromatin interactions.

9. The method according to any one of the preceding aspects, further comprising: generating, by the one or more processors, a network of spatial interactions for a particular set of loci.

10. The method according to any one of the preceding aspects, wherein identifying the subset of pairwise contacts within each bin pair includes identifying the subset of pairwise contacts within each bin pair using a binary search tree.

11. The method according to any one of the preceding aspects, wherein the first set of the plurality of bins and the second set of the plurality of bins are the same bins corresponding to a same chromosome.

12. The method according to any one of the preceding aspects, wherein each genomic element corresponds to a locus within a genome; and wherein each bin corresponds to a contiguous segment of deoxyribonucleic acid (DNA) sequence including at least one of: a topologically associating domain (TAD), a gene, a chromatin state segment, a loop domain, or a chromatin domain.

13. The method according to any one of the preceding aspects, wherein identifying a first set of the plurality of bins and a second set of the plurality of bins includes receiving a selection of the first and second sets of bins to perform a genome-wide search for long range interactions, a genome-wide mapping of regulatory circuits, a comprehensive evaluation of inter-cell-type variability in long range interactions, or identify a set of Hi-C based diagnostic and prognostic biomarkers.

14. The method according to any one of the preceding aspects, further comprising: for one or more of the bin pairs, comparing, by the one or more processors, an actual density for the bin pair from a first bio-cellular system or physiological condition to an actual density for the bin pair from a second bio-cellular system or physiological condition to identify differential contacts.

15. A computing device for analyzing spatial and temporal organization of chromatin, the computing device comprising: a communication network, one or more processors; and a non-transitory computer-readable memory coupled to the one or more processors and storing thereon instructions that, when executed by the one or more processors, cause the computing device to: obtain a set of pairwise contacts of genomic elements; segment genomic elements into a plurality of bins, wherein bin sizes for the plurality of bins are non-uniform; identify a first set of the plurality of bins and a second set of the plurality of bins; generate a matrix of n×m bin pairs, wherein n corresponds to the first set of the plurality of bins and m corresponds to the second set of the plurality of bins; identify a subset of pairwise contacts within each of the bin pairs; determine an interaction frequency for each of the bin pairs; normalize each of the interaction frequencies to generate a normalized interaction frequency for each bin pair; and provide, via the communication network, a mapping of chromatin interactions for display on a user interface, including indications of the bin pairs and respective indications of normalized interaction frequencies.

16. The computing device according to aspect 15, wherein to normalize each of the interaction frequencies, the instructions cause the computing device to: determine a density of the set of pairwise contacts as a function of genomic distance to generate a density function; for each of the plurality of bin pairs: integrate the density function over an area of the bin pair to determine an expected density for the bin pair; compare the subset of pairwise contacts within the bin pair to the expected density for the bin pair by performing a statistical analysis using a Poisson statistical distribution to determine a likelihood that an amount in which an actual density for the bin pair is greater than the expected density for the bin pair is significantly significant; apply false discovery rate for multiple comparison control to the determined likelihood to determine an adjusted likelihood; and when the adjusted likelihood is less than a threshold likelihood, determine that the bin pair has enriched contacts, wherein the density function is generated from empirical data and at least a portion of the density function decreases as genomic distance increases.

17. The computing device according to either one of aspect 15 or aspect 16, wherein the instructions further cause the computing device to: identify individual loci of DNA sequence associated with or causatively associated with one or more molecular phenotypes; identify a set of bins containing the individual loci; obtain chromatin interaction data for a subject; compare the chromatin interaction data for the bins containing the individual loci to contact data on such bins in another bio-cellular system; and predict molecular phenotypes for the subject based on the comparison.

18. The computing device according to any one of aspects 15-17, wherein the instructions further cause the computing device to: generate a 3D or 4D model of chromosome structures based on the mapping of chromatin interactions; or generate a network of spatial interactions for a particular set of loci.

19. The computing device according to any one of aspects 15-18, wherein the subset of pairwise contacts within each bin pair are identified using a binary search tree, wherein the first set of the plurality of bins and the second set of the plurality of bins are the same bins corresponding to a same chromosome, wherein each genomic element corresponds to a locus within a genome, and wherein each bin corresponds to a contiguous segment of deoxyribonucleic acid (DNA) sequence including at least one of: a topologically associating domain (TAD), a gene, a chromatin state segment, a loop domain, or a chromatin domain.

20. The computing device according to any one of aspects 15-19, wherein to identify a first set of the plurality of bins and a second set of the plurality of bins, the instructions cause the computing device to receive a selection of the first and second sets of bins to perform a genome-wide search for long range interactions, a genome-wide mapping of regulatory circuits, a comprehensive evaluation of inter-cell-type variability in long range interactions, or identify a set of Hi-C based diagnostic and prognostic biomarkers.

We claim:

1. A computer-implemented method for analyzing spatial and temporal organization of chromatin, the method executed by one or more processors programmed to perform the method, the method comprising:
   obtaining, at one or more processors, a set of pairwise contacts of genomic elements;
   sorting, by the one or more processors, genomic elements into a plurality of bins, wherein bin sizes for the plurality of bins are non-uniform;
   identifying, by the one or more processors, a first set of the plurality of bins for a first and a second set of the plurality of bins;
   generating, by the one or more processors, a matrix of n×m bin pairs, wherein n is a count of the first set of the plurality of bins and m is a count of the second set of the plurality of bins;
   storing, by the one or more processors, the matrix of n×m bin pairs having non-uniform bin sizes in a memory;
   identifying, by the one or more processors, a subset of pairwise contacts within each of the bin pairs;
   determining, by the one or more processors, an interaction frequency for each of the bin pairs;
   normalizing, by the one or more processors, each of the interaction frequencies to generate a normalized interaction frequency for each bin pair by:
      determining, by the one or more processors, a density of the set of pairwise contacts as a function of genomic distance to generate a density function;
      for each of the plurality of bin pairs:
         integrating, by the one or more processors, the density function over an area of the bin pair to determine an expected density for the bin pair;
         comparing, by the one or more processors, the subset of pairwise contacts within the bin pair to the expected density for the bin pair by performing a statistical analysis using a Poisson distribution to determine a likelihood that an amount in which an actual density for the bin pair is greater than the expected density for the bin pair is statistically significant;
         applying, by the one or more processors, a false discovery rate for multiple comparison control to the determined likelihood to determine an adjusted likelihood; and
         when the adjusted likelihood is less than a threshold likelihood, determining, by the one or more processors, that the bin pair has enriched contacts; and
   providing, by the one or more processors, a mapping of chromatin interactions for display on a user interface, including indications of the bin pairs and respective indications of normalized interaction frequencies.

2. The method of claim 1, further comprising:
   performing, by the one or more processors, a statistical analysis using the Poisson distribution to determine a second likelihood that the amount in which the actual density for the bin pair is less than the expected density for the bin pair is statistically significant;
   applying, by the one or more processors, a false discovery rate for multiple comparison control to the determined second likelihood to determine an adjusted second likelihood; and
   when the adjusted second likelihood is less than a threshold likelihood, determining, by the one or more processors, that the bin pair has depleted contacts.

3. The method of claim 2, wherein the statistical analysis includes a two-tailed test to determine a third likelihood that the amount in which the actual density for the bin pair differs from the expected density is statistically significant;
   applying, by the one or more processors, a false discovery rate for multiple comparison control to the determined third likelihood to determine an adjusted third likelihood; and
   when the adjusted third likelihood is less than a threshold likelihood, determining, by the one or more processors, that the bin pair has enriched or depleted contacts.

4. The method of claim 1,
   wherein at least some of the pairwise contacts are trans contacts, such that both genomic elements in each of the at least some pairwise contacts correspond to different chromosomes.

5. The method of claim 1, wherein the density function is generated from empirical data and at least a portion of the density function decreases as genomic distance increases.

6. The method of claim 1, further comprising:
   identifying, by the one or more processors, individual loci of DNA sequence associated with or causatively associated with one or more molecular phenotypes;
   identifying, by the one or more processors, a set of bins containing the individual loci;
   obtaining, by the one or more processors, chromatin interaction data for a subject;
   comparing, by the one or more processors, the chromatin interaction data for the bins containing the individual loci to contact data on such bins in another bio-cellular system; and
   predicting, by the one or more processors, molecular phenotypes for the subject based on the comparison.

7. The method of claim 1, further comprising:
   generating, by the one or more processors, a 3D or 4D model of chromosome structures based on the mapping of chromatin interactions.

8. The method of claim 1, further comprising:
   generating, by the one or more processors, a network of spatial interactions for a particular set of loci.

9. The method of claim 1, wherein identifying the subset of pairwise contacts within each bin pair includes identifying the subset of pairwise contacts within each bin pair using a binary search tree.

10. The method of claim 1, wherein each genomic element corresponds to a locus within a genome; and
    wherein each bin corresponds to a contiguous segment of deoxyribonucleic acid (DNA) sequence including at least one of: a topologically associating domain (TAD), a gene, a chromatin state segment, a loop domain, or a chromatin domain.

11. The method of claim 10, wherein identifying a first set of the plurality of bins and a second set of the plurality of bins includes receiving a selection of the first and second sets of bins to perform a genome-wide search for long range interactions, a genome-wide mapping of regulatory circuits, a comprehensive evaluation of inter-cell-type variability in long range interactions, or identify a set of Hi-C based diagnostic and prognostic biomarkers.

12. The method of claim 1, further comprising:
for one or more of the bin pairs, comparing, by the one or more processors, an actual density for the bin pair from a first bio-cellular system or physiological condition to an actual density for the bin pair from a second bio-cellular system or physiological condition to identify differential contacts.

13. A computing device for analyzing spatial and temporal organization of chromatin, the computing device comprising:
a communication network,
one or more processors; and
a non-transitory computer-readable memory coupled to the one or more processors and storing thereon instructions that, when executed by the one or more processors, cause the computing device to:
obtain a set of pairwise contacts of genomic elements;
sort genomic elements into a plurality of bins, wherein bin sizes for the plurality of bins are non-uniform;
identify a first set of the plurality of bins and a second set of the plurality of bins;
generate a matrix of n×m bin pairs, wherein n is a count of the first set of the plurality of bins and m is a count of the second set of the plurality of bins;
store the matrix of n×m bin pairs having non-uniform bin sizes in the memory;
identify a subset of pairwise contacts within each of the bin pairs;
determine an interaction frequency for each of the bin pairs;
normalize each of the interaction frequencies to generate a normalized interaction frequency for each bin pair by:
determining a density of the set of pairwise contacts as a function of genomic distance to generate a density function;
for each of the plurality of bin pairs:
integrating the density function over an area of the bin pair to determine an expected density for the bin pair;
comparing the subset of pairwise contacts within the bin pair to the expected density for the bin pair by performing a statistical analysis using a Poisson distribution to determine a likelihood that an amount in which an actual density for the bin pair is greater than the expected density for the bin pair is statistically significant;
applying a false discovery rate for multiple comparison control to the determined likelihood to determine an adjusted likelihood; and
when the adjusted likelihood is less than a threshold likelihood, determining that the bin pair has enriched contacts; and
provide, via the communication network, a mapping of chromatin interactions for display on a user interface, including indications of the bin pairs and respective indications of normalized interaction frequencies.

14. The computing device of claim 13, wherein the instructions further cause the computing device to:
identify individual loci of DNA sequence associated with or causatively associated with one or more molecular phenotypes;
identify a set of bins containing the individual loci;
obtain chromatin interaction data for a subject;
compare the chromatin interaction data for the bins containing the individual loci to contact data on such bins in another bio-cellular system; and
predict molecular phenotypes for the subject based on the comparison.

15. The computing device of claim 13, wherein the instructions further cause the computing device to:
generate a 3D or 4D model of chromosome structures based on the mapping of chromatin interactions; or
generate a network of spatial interactions for a particular set of loci.

16. The computing device of claim 13, wherein the subset of pairwise contacts within each bin pair are identified using a binary search tree, wherein each genomic element corresponds to a locus within a genome, and wherein each bin corresponds to a contiguous segment of deoxyribonucleic acid (DNA) sequence including at least one of: a topologically associating domain (TAD), a gene, a chromatin state segment, a loop domain, or a chromatin domain.

17. The method of claim 1, further comprising:
performing a genome-wide search for long range interactions using the mapping of chromatin interactions.

* * * * *

UNITED STATES PATENT AND TRADEMARK OFFICE
CERTIFICATE OF CORRECTION

| | | |
|---|---|---|
| PATENT NO. | : 12,154,661 B2 | Page 1 of 1 |
| APPLICATION NO. | : 16/359385 | |
| DATED | : November 26, 2024 | |
| INVENTOR(S) | : Ari Allyn-Feuer et al. | |

It is certified that error appears in the above-identified patent and that said Letters Patent is hereby corrected as shown below:

In the Claims

At Column 29, Line 23, "bins for a first" should be -- bins --.

Signed and Sealed this
Tenth Day of June, 2025

Coke Morgan Stewart
*Acting Director of the United States Patent and Trademark Office*